US008637083B2

(12) United States Patent
Troiano et al.

(10) Patent No.: US 8,637,083 B2
(45) Date of Patent: *Jan. 28, 2014

(54) STABLE FORMULATIONS FOR LYOPHILIZING THERAPEUTIC PARTICLES

(71) Applicant: BIND Therapeutics, Inc., Cambridge, MA (US)

(72) Inventors: Greg Troiano, Pembroke, MA (US); Young-Ho Song, Natick, MA (US); Stephen E. Zale, Hopkinton, MA (US); James Wright, Lexington, MA (US); Christina Van Geen Hoven, Cambridge, MA (US)

(73) Assignee: BIND Therapeutics, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/916,133

(22) Filed: Jun. 12, 2013

(65) Prior Publication Data

US 2013/0295183 A1    Nov. 7, 2013

Related U.S. Application Data

(63) Continuation of application No. 13/862,090, filed on Apr. 12, 2013, which is a continuation of application No. 13/664,133, filed on Oct. 30, 2012, which is a continuation of application No. 12/965,294, filed on Dec. 10, 2010, now Pat. No. 8,357,401.

(60) Provisional application No. 61/285,722, filed on Dec. 11, 2009.

(51) Int. Cl.
  *A61K 9/14* (2006.01)
  *A61K 9/19* (2006.01)
  *A61K 33/14* (2006.01)
  *A61K 31/724* (2006.01)
  *A61K 47/30* (2006.01)
  *A61K 47/40* (2006.01)

(52) U.S. Cl.
  USPC ........... 424/489; 424/677; 424/678; 424/680; 514/53; 514/58; 514/772.3; 977/773; 977/904; 977/906; 977/915

(58) Field of Classification Search
  None
  See application file for complete search history.

(56) References Cited

U.S. PATENT DOCUMENTS

| | | | |
|---|---|---|---|
| 5,302,401 A | 4/1994 | Liversidge et al. | |
| 5,543,158 A | 8/1996 | Gref et al. | |
| 5,563,122 A | 10/1996 | Endo et al. | |
| 5,578,325 A | 11/1996 | Domb et al. | |
| 5,766,635 A | 6/1998 | Spenleuhauer et al. | |
| 6,007,845 A | 12/1999 | Domb et al. | |
| 6,136,846 A | 10/2000 | Rubinfeld et al. | |
| 6,139,870 A | 10/2000 | Verrecchia | |
| 6,201,072 B1 | 3/2001 | Rathi et al. | |
| 6,254,890 B1 | 7/2001 | Hirosue et al. | |
| 6,265,609 B1 | 7/2001 | Jackson et al. | |
| 6,346,274 B1 | 2/2002 | Koll et al. | |
| 6,395,718 B1 | 5/2002 | Slusher et al. | |
| 6,528,499 B1 | 3/2003 | Kozikowski et al. | |
| 6,841,547 B2 | 1/2005 | Brown et al. | |
| 6,875,886 B2 | 4/2005 | Frangioni | |
| 6,890,950 B2 | 5/2005 | Boothman et al. | |
| 6,902,743 B1 | 6/2005 | Setterstrom et al. | |
| 6,916,788 B2 | 7/2005 | Seo et al. | |
| 7,422,902 B1 | 9/2008 | Wheeler et al. | |
| 8,003,128 B2 | 8/2011 | Kreuter et al. | |
| 8,034,765 B2 | 10/2011 | De et al. | |
| 8,206,747 B2 | 6/2012 | Zale et al. | |
| 8,211,473 B2 | 7/2012 | Troiano et al. | |
| 8,236,330 B2 | 8/2012 | Zale et al. | |
| 8,246,968 B2 | 8/2012 | Zale et al. | |
| 8,273,363 B2 | 9/2012 | Zale et al. | |
| 8,293,276 B2 | 10/2012 | Troiano et al. | |
| 8,318,208 B1 | 11/2012 | Zale et al. | |
| 8,318,211 B2 | 11/2012 | Zale et al. | |
| 8,357,401 B2 | 1/2013 | Troiano et al. | |
| 8,420,123 B2 | 4/2013 | Troiano et al. | |
| 2002/0045582 A1 | 4/2002 | Margolin et al. | |
| 2002/0119916 A1 | 8/2002 | Hassan | |
| 2003/0068377 A1 | 4/2003 | Fowers et al. | |
| 2003/0143184 A1 | 7/2003 | Seo et al. | |
| 2003/0232887 A1 | 12/2003 | Johnson et al. | |
| 2003/0235619 A1 | 12/2003 | Allen et al. | |
| 2004/0054190 A1 | 3/2004 | Pomper et al. | |
| 2004/0071768 A1 | 4/2004 | Sarris et al. | |
| 2004/0081688 A1 | 4/2004 | Del Curto et al. | |

(Continued)

FOREIGN PATENT DOCUMENTS

| CN | 101053553 A | 10/2007 |
|---|---|---|
| EA | 011594 | 12/2007 |

(Continued)

OTHER PUBLICATIONS

Altmann (Epothilone B and its analogs—a new family of anticancer agents, *Mini Rev Med Chem.* (2003) 3(2):149-158; Abstract Only [retrieved from Bentham Science, < URL: http://www.eurekaselect.com/80911/artcile>], 1 page.

Altmann (Epothilone B and its analogs—a new family of anticancer agents, *Mini Rev Med Chem.* (2003) 3(2):149-158; Abstract Only [retrieved from PUBMED, < URL: http://www.ncbi.nlm.nih.gov/pubmed/12570848>]), 1 page.

Extended European Search Report for EP 09794913.5 mailed Jul. 4, 2013, 9 pages.

Extended European Search Report for EP 10842556.2 mailed Jul. 8, 2013, 9 pages.

(Continued)

*Primary Examiner* — Ernst Arnold
(74) *Attorney, Agent, or Firm* — Goodwin Procter LLP

(57) ABSTRACT

The present disclosure generally relates to lyophilized pharmaceutical compositions comprising polymeric nanoparticles which, upon reconstitution, have low levels of greater than 10 micron size particles. Other aspects of the invention include methods of making such nanoparticles.

19 Claims, 15 Drawing Sheets

(56) References Cited

U.S. PATENT DOCUMENTS

| | | |
|---|---|---|
| 2004/0086544 A1 | 5/2004 | Bezemer et al. |
| 2004/0185170 A1 | 9/2004 | Chungi et al. |
| 2004/0219224 A1 | 11/2004 | Yakovlevsky et al. |
| 2004/0220081 A1 | 11/2004 | Kreitz et al. |
| 2004/0247624 A1 | 12/2004 | Unger et al. |
| 2004/0247680 A1 | 12/2004 | Farokhzad et al. |
| 2005/0037075 A1 | 2/2005 | Farokhzad et al. |
| 2005/0037086 A1 | 2/2005 | Tyo et al. |
| 2005/0063976 A1 | 3/2005 | Schultes et al. |
| 2005/0123617 A1 | 6/2005 | Chang et al. |
| 2005/0136258 A1 | 6/2005 | Nie et al. |
| 2005/0142205 A1 | 6/2005 | Rashba-Step et al. |
| 2005/0201972 A1 | 9/2005 | Seo et al. |
| 2005/0256071 A1 | 11/2005 | Davis |
| 2005/0266067 A1 | 12/2005 | Sengupta et al. |
| 2006/0002852 A1 | 1/2006 | Saltzman et al. |
| 2006/0002971 A1 | 1/2006 | Saltzman et al. |
| 2006/0034925 A1 | 2/2006 | Au et al. |
| 2006/0057219 A1 | 3/2006 | Nagasaki et al. |
| 2006/0110460 A1 | 5/2006 | Ferret et al. |
| 2006/0165987 A1 | 7/2006 | Hildgen et al. |
| 2007/0031402 A1 | 2/2007 | Zhang et al. |
| 2007/0041901 A1 | 2/2007 | Diener et al. |
| 2007/0043066 A1 | 2/2007 | Sum et al. |
| 2007/0053845 A1 | 3/2007 | Sengupta et al. |
| 2007/0154554 A1 | 7/2007 | Burgermeister et al. |
| 2008/0057102 A1 | 3/2008 | Roorda |
| 2008/0081074 A1 | 4/2008 | Gu et al. |
| 2008/0124400 A1 | 5/2008 | Liggins et al. |
| 2008/0193381 A1 | 8/2008 | Babich et al. |
| 2008/0267876 A1 | 10/2008 | Benita et al. |
| 2009/0053293 A1 | 2/2009 | Liang et al. |
| 2009/0053315 A1 | 2/2009 | Brough et al. |
| 2009/0061009 A1 | 3/2009 | Schwarz et al. |
| 2009/0061010 A1 | 3/2009 | Zale et al. |
| 2009/0074753 A1 | 3/2009 | Lynch |
| 2009/0074828 A1 | 3/2009 | Alexis et al. |
| 2009/0155349 A1 | 6/2009 | Heller et al. |
| 2009/0170753 A1 | 7/2009 | Welz et al. |
| 2009/0306120 A1 | 12/2009 | Lim et al. |
| 2009/0317479 A1 | 12/2009 | Ishihara et al. |
| 2010/0008998 A1 | 1/2010 | Kang et al. |
| 2010/0015050 A1 | 1/2010 | Panyam et al. |
| 2010/0040537 A1 | 2/2010 | Gu et al. |
| 2010/0068285 A1 | 3/2010 | Zale et al. |
| 2010/0068286 A1 | 3/2010 | Troiano et al. |
| 2010/0069426 A1 | 3/2010 | Zale et al. |
| 2010/0087337 A1 | 4/2010 | Dewitt |
| 2010/0104645 A1 | 4/2010 | Ali et al. |
| 2010/0104655 A1 | 4/2010 | Zale et al. |
| 2010/0166866 A1 | 7/2010 | Fischer et al. |
| 2010/0216804 A1 | 8/2010 | Zale et al. |
| 2010/0226986 A1 | 9/2010 | Grayson et al. |
| 2010/0266491 A1 | 10/2010 | Farokhzad et al. |
| 2010/0303723 A1 | 12/2010 | Farokhzad et al. |
| 2010/0303900 A1 | 12/2010 | Ramstack et al. |
| 2010/0316725 A1 | 12/2010 | Ryde et al. |
| 2011/0159079 A1 | 6/2011 | Li et al. |
| 2011/0217377 A1 | 9/2011 | Zale et al. |
| 2011/0224288 A1 | 9/2011 | Zale et al. |
| 2011/0274759 A1 | 11/2011 | Troiano et al. |
| 2011/0275704 A1 | 11/2011 | Troiano et al. |
| 2011/0294717 A1 | 12/2011 | Ali et al. |
| 2012/0004293 A1 | 1/2012 | Zale et al. |
| 2012/0027820 A1 | 2/2012 | Troiano et al. |
| 2012/0140790 A1 | 6/2012 | Ali et al. |
| 2012/0276162 A1 | 11/2012 | Zale et al. |
| 2013/0034608 A1 | 2/2013 | Zale et al. |
| 2013/0108668 A1 | 5/2013 | Figueiredo et al. |
| 2013/0115293 A1 | 5/2013 | Sabnis et al. |
| 2013/0172406 A1 | 7/2013 | Zale et al. |

FOREIGN PATENT DOCUMENTS

| | | |
|---|---|---|
| EP | 0805678 A1 | 11/1997 |
| EP | 1985309 A1 | 10/2008 |
| EP | 2106806 A1 | 10/2009 |
| KR | 10-0418916 | 3/2002 |
| KR | 20020041712 A | 6/2002 |
| RU | 2007/140909 A | 5/2009 |
| WO | WO-95/03357 A1 | 2/1995 |
| WO | WO-00/00222 A1 | 1/2000 |
| WO | WO-02/080846 A2 | 10/2002 |
| WO | WO-02/098885 A1 | 12/2002 |
| WO | WO-03/017987 A1 | 3/2003 |
| WO | WO-03/055469 A1 | 7/2003 |
| WO | WO-03/086369 A2 | 10/2003 |
| WO | WO-2004/084871 A1 | 10/2004 |
| WO | WO-2004/089291 A2 | 10/2004 |
| WO | WO-2005/020989 A1 | 3/2005 |
| WO | WO-2005/046572 A2 | 5/2005 |
| WO | WO-2006/093991 A1 | 9/2006 |
| WO | WO-2007/024323 A2 | 3/2007 |
| WO | WO-2007/028341 A1 | 3/2007 |
| WO | WO-2007/034479 A2 | 3/2007 |
| WO | WO-2007/074604 A1 | 7/2007 |
| WO | WO-2007/110152 A2 | 10/2007 |
| WO | WO-2007/133807 A2 | 11/2007 |
| WO | WO-2008/019142 A2 | 2/2008 |
| WO | WO-2008/058192 A2 | 5/2008 |
| WO | WO-2008/105773 A2 | 9/2008 |
| WO | WO-2008/121949 A1 | 10/2008 |
| WO | WO-2008/124632 A1 | 10/2008 |
| WO | WO-2008/124634 A1 | 10/2008 |
| WO | WO-2008/124639 A2 | 10/2008 |
| WO | WO-2008/139804 A1 | 11/2008 |
| WO | WO-2009/070302 A1 | 6/2009 |
| WO | WO-2009/074274 A1 | 6/2009 |
| WO | WO-2009/084801 A1 | 7/2009 |
| WO | WO-2010/005721 A2 | 1/2010 |
| WO | WO-2010/005723 A2 | 1/2010 |
| WO | WO-2010/005725 A2 | 1/2010 |
| WO | WO-2010/005726 A2 | 1/2010 |
| WO | WO-2010/068866 A2 | 6/2010 |
| WO | WO-2010/075072 A2 | 7/2010 |
| WO | WO-2010/114768 A1 | 10/2010 |
| WO | WO-2010/114770 A1 | 10/2010 |
| WO | WO-2010/117668 A1 | 10/2010 |
| WO | WO-2011/072218 A2 | 6/2011 |
| WO | WO-2011/079279 A2 | 6/2011 |
| WO | WO-2011/084513 A2 | 7/2011 |
| WO | WO-2011/084518 A2 | 7/2011 |
| WO | WO-2011/084521 A2 | 7/2011 |
| WO | WO-2011/119995 A2 | 9/2011 |
| WO | WO-2012/054923 A2 | 4/2012 |
| WO | WO-2012/166925 A2 | 12/2012 |
| WO | WO-2013/044219 A1 | 3/2013 |

OTHER PUBLICATIONS

Extended European Search Report for EP 10842557.0 mailed Jul. 8, 2013, 11 pages.

Extended European Search Report for EP 10842554.7 mailed Jul. 10, 2013, 9 pages.

Gref et al., "'Stealth' Corona-Core Nanoparticles Surface Modified by Polyethylene Glycol (PEG): Influences of the Corona (PEG Chain Length and Surface Density) and of the Core Composition on Phagocytic Uptake and Plasma Protein Adsorption," *Colloids and Surfaces B: Biointerfaces*. (2000) 301-313.

International Preliminary Report on Patentability for PCT/US2010/060575 dated Jun. 19, 2012, 11 pages.

Matsumoto et al., "Preparation of Nanoparticles consisted of poly(L-lactide)-poly(ethylene glycol)poly(L-lactide) and Their Evaluation In Vitro," *International J. of Pharmaceutics*. (1999) 185:93-101.

Merck (Betamethasone, Merck Index (Knovel, copyright 2006, 2012)), 3 pages.

Abdelwahed et al., "Freeze-Drying of Nanoparticles: Formulation, Process and Storage Considerations," *Adv. Drug Deliv. Rev.* (2006) 58:1688-1713.

Abizaid et al., "Sirolimus-Eluting Stents Inhibits Neointimal Hyperplasia in Diabetic Patients," *Eur. Heart J.* (2006) 25:104-112.

(56) References Cited

OTHER PUBLICATIONS

Adams et al., "Amphiphilic Block Copolymers for Drug Delivery", *J. Pharm. Sci.* (2003) 92, 1343-1355.
Barinka et al., "Interactions Between Human Glutamate Carboxypeptidase II and Urea-Based Inhibitors: Structural Characterization," *J. Med. Chem.* (2008) 51:7737-7743.
Barinka et al., "Structural Insight into the Pharmacophore Pocket of Human Glutamate Carboxypeptidase II," *J. Med. Chem.* (2007) 50:3267-3273.
Bilati et al., "Nanoprecipitation Versus Emulsion-based Techniques for the Encapsulation of Proteins into Biodegradable Nanoparticles and Process-related Stability Issues," AAPS *PharmSciTech.* (2005) 6(4):E594-E604.
Blindt et al., "A Novel Drug-Eluting Stent Coated with an Integrin-Binding Cyclic Arg-Gly-Asp Peptide Inhibits Neointimal Hyperplasia by Recruiting Endothelial Progenitor Cells," *J. Amer. Coll. Cardiol.* (2006) 47(9):1786-1795.
Caliceti et al., "Effective Protein Release from PEG/PLA Nanoparticles Produced by Compressed Gas Anti-Solvent Precipitation Techniques," *Journal of Controlled Release.* (2004) 94:195-205.
Chandran, et al., "Characterization of a Targeted Nanoparticle Functionalized with a Urea-Based Inhibitor of Prostate-Specific Membrane Antigen (PSMA)," *Cancer Biol. Ther.* (2008) 7:4:1-9.
Chen et al., "Radiohalogenated Prostate-Specific Membrane Antigen (PSMA)-Based Ureas as Imaging Agents for Prostate Cancer," *J. Med. Chem.* (2008) 51(24):7933-7943.
Cheng et al., "Formulation of Functionalized PLGA-PEG Nanoparticles for in Vivo Targeted Drug Delivery," *Biomaterials.* (2007) 28:869-879.
Dancey et al., "Therapeutic Targets" mTOR and Related Pathways, *Cancer Biol. Ther.* (2006) 5:9: 1065-1073.
Davaran, "Preparation and in Vitro Evaluation of Linear and Star-Branched PLGA Nanoparticles for Insulin Delivery," *J. Bioact. Compat. Polym.* (2008) 23:115-131.
De Jaeghere et al., "Formulation and Lyoprotection of Poly(lactic acid-co-ethylene oxide) Nanoparticles: Influence on Physical Stability and in Vitro Cell Uptake," *Pharm. Res.* (1999) 16(6):859-866.
De Jaeghere et al., "Freeze-Drying and Lyopreservation of Diblock and Triblock Poly(Lactic Acid)-Poly(Ethylene Oxide) (PLA-PEO) Copolymer Nanoparticles," *Pharmaceutical Development and Technology.* (2000) 5(4):473-483.
"Docetaxel Dosage," [retrieved on Mar. 28, 2013] http://www.drugs.com/dosage/docetaxel.html.
Eurasian Search Report for Application No. EA 201170038, dated Jul. 8, 2011.
Eurasian Search Report for Application No. EA 201170039, dated Nov. 21, 2011.
Ewesuedo et al., "Chapter 1: Systemically Administered Drugs." *Drug Delivery Systems in Cancer Therapy.* Ed. D.M. Brown. Totowa:Humana, 2003, pp. 3-14.
Extended European Search Report for Application No. EP 09794913.5 mailed Jul. 8, 2011.
Extended European Search Report for Application No. EP 09794915.0, mailed Jan. 25, 2012.
Extended European Search Report for Application No. EP 09835578.7, mailed May 18, 2012.
Extended European Search Report for Application No. EP 11186037.5, mailed Mar. 2, 2012.
Extended European Search Report for Application No. EP 10836748.3, mailed Mar. 21, 2013.
Farokhzad et al., "Nanoparticle-Aptamer Bioconjugates: A New Approach for Targeting Prostate Cancer Cells," *Cancer Res.* (Nov. 1, 2004) 64:7668-7672.
Farokhzad et al., "Targeted Nanoparticle-Aptamer Bioconjugates for Cancer Chemotherapy In Vivo," *Proc. Natl. Acad. Sci. USA.* (2006) 103(16):6315-6320.
Feng et al., "Nanoparticles of Biodegradable Polymers for Clinical Administration of Paclitaxel," *Current Medicinal Chemistry.* (2004) 11:413-424.

Foss et al., "Radiolabeled Small-Molecule Ligands for Prostate-Specific Membrane Antigen: In Vivo Imaging in Experimental Models of Prostate Cancer," *Clin. Cancer Res.* (2005) 11(11): 4022-4028.
Foss, Poster Session: Novel Probes and Activation Strategies, Part 3, "Synthesis and Validation of a Novel Small-Molecule Fluorescent Probe for PSMA Expression in Human Tumor Neovasculature," 4th Annual Meeting for the Society for Molecular Imaging, (Sep. 7-10, 2005.).
Fournier et al., "Experimental Studies and Preliminary Clinical Trial of Vinorelbine-loaded Polymeric Bioresorbable Implants for the Local Treatment of Solid Tumors," *Cancer Research.* (1991) 51:5384-5391.
Galsky et al., "Cabazitaxel," *Nature Reviews.* (2010) 9:677-678.
Gao et al., "In Vivo Cancer Targeting and Imaging with Semiconductor Quantum Dots," *Nat. Biotechnol.* (2004) 22, 8: 969-976.
Gill et al., "Modulated Differential Scanning Calorimetry," J. Thermal Analysis. (1993) 40:931-939.
Govender et al., "Defining the Drug Incorporation Properties of PLA-PEG Nanoparticles," *Int. J. Pharm.* (2000) 199:95-110.
Gref et al., "Biodegradable Long-Circulating Polymeric Nanospheres," *Science.* (1994) 263:1600-1603.
Gref et al., "Development and Characterization of CyA-loaded Poly(lactic acid)-poly(ethylene glycol)PEG Micro- and Nanoparticles. Comparison with Conventional PLA Particulate Carriers." *Eur. J. Pharm. Biopharm.* (2001) 51:111-118.
Gu et al., "Precise Engineering of Targeted Nanoparticles by Using Self-Assembled Biointegrated Block Copolymers", *Proc. Natl. Acad. Sci. USA.* (2008) 105:2586-2591.
Heald et al., "Poly(lactic acid)-Poly(ethylene oxide) (PLA-PEG) Nanoparticles: NMR Studies of the Central Solidlike PLA Core and the Liquid PEG Corona," *Langmuir.* (2002) 18:3669-3675.
Hederstrom et al., "Purification and Surface Modification of Polymeric Nanoparticles for Medical Applications" Master's Thesis. SINTEF Materials and Chemistry, Trondheim, Norway, Mar. 3, 2008.
Heldman et al., "Paclitaxel stent coating inhibits neointimal hyperplasia at 4 weeks in a porcine model of coronary restenosis," *Circulation.* (2001) 103:2289-2295.
Hrkach et al., "Preclinical Development and Clinical Translation of a PSMA-Targeted Docetaxel Nanoparticle with a Differentiated Pharmacological Profile," *Sci. Trans. Med.* (2012) 4:1-11.
Humblet et al., "An HPLC/Mass Spectrometry Platform for the Development of Multimodality Contrast Agents and Targeted Therapeutics: Prostate-Specific Membrane Antigen Small Molecule Derivatives," *Contrast Med. Mol. Imaging.* (2006) 1:196-211.
Humblet et al., "High-Affinity Near-Infrared Fluorescent Small-Molecule Contrast Agents for In Vivo Imaging of Prostate-Specific Membrane Antigen," *Mol. Imaging.* ( 2005) 4:448-462.
International Search Report for Application No. PCT/US08/13158 dated Jan. 20, 2009 and mailed Feb. 17, 2009.
International Search Report for Application No. PCT/US08/58873 dated Aug. 15, 2008 and mailed Aug. 28, 2008.
International Search Report for Application No. PCT/US09/47513 dated Jan. 18, 2010 and mailed Jan. 18, 2010.
International Search Report for Application No. PCT/US09/67672 dated Aug. 20, 2010 and mailed Aug. 23, 2010.
International Search Report for Application No. PCT/US09/68028 dated Aug. 9, 2010 and mailed Aug. 23, 2010.
International Search Report for Application No. PCT/US10/59879 dated Aug. 30, 2011 and mailed Aug. 30, 2011.
International Search Report for Application No. PCT/US10/60564 dated Sep. 29, 2011 and mailed Sep. 29, 2011.
International Search Report for Application No. PCT/US10/60570 dated Aug. 25, 2011 and mailed Aug. 25, 2011.
International Search Report for Application No. PCT/US10/60575 dated Aug. 25, 2011 and mailed Aug. 25, 2011.
International Search Report for Application No. PCT/US11/057498 dated May 9, 2012 and mailed May 10, 2012.
International Search Report for Application No. PCT/US2012/040215 dated Nov. 16, 2012 and mailed Nov. 16, 2012.
International Search Report for Application No. PCT/US2012/056891 dated Jan. 4, 2013 and mailed Jan. 4, 2013.

(56) References Cited

OTHER PUBLICATIONS

International Search Report for PCT/US09/47515 dated Jan. 18, 2010 and mailed Jan. 19, 2010.
International Search Report for PCT/US09/47517 dated Feb. 23, 2010 and mailed Mar. 2, 2010.
International Search Report for PCT/US09/47518 dated Mar. 5, 2010 and mailed Mar. 5, 2010.
Jayaprakash et al., "Design and Synthesis of a PSMA Inhibitor-Doxorubicin Conjugate for Targeted Prostate Cancer Therapy," ChemMedChem 2006, 1, pp. 299-302.
Jeong et al., "Effect of cryoprotectants on the reconstitution of surfactant-free nanoparticles of poly(DL-lactide-co-glycolide)," *J. of Microencapsulation.* (2005) 22(6):593-601.
Jiang et al., "Preparation of PLA and PLGA Nanoparticles by Binary Organic Solvent Diffusion Method," *J. Cent. South Univ. Technol.* (2003) 10(3):202-206.
Konstantinos Avgoustakis, "Pegylated poly(lactide) and poly(lactide-co-glycolide) nanoparticles: Preparation, properties and possible applications in drug delivery," *Current Drug Delivery.* (2004) 1(4):321-333.
Koziara et al., "Blood Compatibility of Cetyl Alcohol/Polysorbate-Based Nanoparticles," *Pharma. Res.* (2005) 22(11):1821-1828.
Kozikowski et al., Design of Remarkably Simple, Yet Potent Urea-Based Inhibitors of Glutamate Carboxypeptidase II (NAALADase), *J. Med. Chem.* (2001) 44:298-301.
Kozikowski et al., "Synthesis of Urea-Based Inhibitors as Active Site Probes of Glutamate Carboxypeptidase II: Efficacy as Analgesic Agents," *J. Med. Chem.* (2004) 47:1729-1738.
Kwon, "Long Acting Porous Microparticle for Pulmonary Protein Delivery," *Int. J. Pharm.* (2007) 333:5-9.
Lyseng-Williamson et al., "Docetaxel A Review of its Use in Metastatic Breast Cancer," *Drugs.* (2005) 65(17):2513-16.
Maresca et al., "A Series of Halogenated Heterodimeric Inhibitors of Prostate Specific Membrane Antigen (PSMA) as Radiolabeled Probes for Targeting Prostate Cancer," *J. Med. Chem.* (2009) 52(2):347-57.
Majer et al., "Synthesis and Biological Evaluation of Thiol-Based Inhibitors of Glutamate Carboxypeptidase II: Discovery of an Orally Active GPC II Inhibitor," *J. Med. Chem.* (2003) 46:1989-1996.
Mease et al., "N-[N-[(S)-1,3-Dicarboxypropyl] Carbamoyl]-4-[18F] Fluorobenzyl-L-Cysteine, [18F] DCFBC: A New Imaging Probe for Prostate Cancer," *Clin. Cancer Res.* (2008) 14(10):3036-3043.
Misra et al., "Production of Multimeric Prostate-Specific Membrane Antigen Small-Molecule Radiotracers Using a Solid-Phase 99m Tc Preloading Strategy," *J. Nuclear Med.* (2007) 48(8):379-1389.
Murugesan et al., Pegylated Poly(lactide-co-glycolidel (PLGA) Nanoparticulate Delivery of Docetaxel: Synthesis of Diblock Copolymers, Optimization of Preparation Variables on Formulation Characteristics and in Vitro Release Studies. *J. Biomed. Nanotechnol.* (2007) 3:52-60.
Musumeci et al., "Lyoprotected Nanosphere Formulations for Paclitaxel Controlled Delivery." *J. Nanosci. Nanotech.* (2006) 6:3118-3125.
Musumeci et al., "PLA/PLGA Nanoparticles for Sustained Release of Docetaxel," *Int. J. Pharm.* (2006) 325:172-179.

Ojer, "Spray-Drying of Poly(anhydride) Nanoparticles for Drug/Antigen Delivery," *J. Drug Del. Sci. Tech.* (2010) 20(5):353-359.
Oliver et al., "Conformational and SAR Analysis of NAALADase and PSMA Inhibitors," *Biorg. Med. Chem.* (2003) 11:4455-4461.
Olivier, "Drug Transport to Brain with Targeted Nanoparticles," *The Journal of the American Society for Experimental NeuroTherapeutics.* (2005) 2:108-119.
Omelczuk et al., "The Influence of Polymer Glass Transition Temperature and Molecular Weight on Drug Release from Tablets Containing Poly(DL-lactic acid)." *Pharm. Res.* (1992) 9(1):26-32.
Peracchia et al., "PEG-coated nanospheres from amphiphilic diblock and multiblock copolymers: Investigation of their drug encapsulation and release characteristics," *Journal of Controlled Release.* (1996) 46:223-231.
Pomper, Martin G., Russell H. Morgan Department of Radiology and Radiological Science, Johns Hopkins University, "New Developments in Molecular Imaging of Prostate Cancer," Topical Symposium on: Advanced Molecular Imaging Techniques in the Detection, Diagnosis, Therapy, and Follow-up of Prostate Cancer, Palazzo Barberini, Rome, Dec. 6, 2005.
Pourcelle, "PCL-PEG-based Nanoparticles Grafted with GRGDS Peptide: Preparation and Surface Analysis by XPS," *Biomacromolecules.* (2007) 8:3977-3983.
Pulkkinen et al., "Three-Step Tumor Targeting of Paclitaxel Using Biotinylated PLA-PEG Nanoparticles and Avidin-Biotin Technology: Formulation Development and In Vitro Anticancer Activity", *Eur. J. Pharm. Biopharm.* (2008) 70:66-74.
Riley et al., "Colloidal Stability and Drug Incorporation Aspects of Micellar-like PLA-PEG Nanoparticles," *Colloids Surf. B: Biointer.* (1999) 16:147-59.
Sapra et al., "Ligand-Targeted Liposomal Anticancer Drugs," *Prog. Lipid Res.* (2003) 42:439-462.
Senthilkumar et al., "Long Circulating PEGylated Poly(D,L-lactide-co-glycolide) Nanoparticulate Delivery of Docetaxel to Solid Tumors," *J. Drug Target.* (2008) 424-435.
Sweetman, "Martindale: The Complete Drug Reference," 33rd ed., 2002, Pharmaceutical Press, entry for Docetaxel, p. 534.
Tamilvanan et al., "Manufacturing Techniques and Excipients Used During the Design of Biodegradable Polymer-Based Microspheres Containing Therapeutic Peptide/Protein for Parenteral Controlled Drug Delivery," *J. Pharm. Sci. Tech.* (2008) 62(2):125-154.
Tang, Hailun, et al., "Prostate Targeting Ligands Based on N-Acetylated α-Linked Acidic Dipeptidase," *Biochem. Biophys. Res. Comm.* 307 (2003), pp. 8-14.
"Taxotere Dosage," [retrieved on Mar. 28, 2013]. http://www.drugs.com/dosage/taxotere.html.
Tobio et al., "Stealth PLA-PEG Nanoparticles as Protein Carriers for Nasal Administration," *Pharm. Res.* (1998) 15(2):270-275.
Vicari et al., "Paclitaxel Loading in PLGA Nanospheres Affected the in Vitro Drug Cell Accumulation and Antiproliferative Activity," *BMC Cancer.* (2008) 8:212.
Yamamoto et al., "Long-Circulating Poly(ethylene glycol)-poly(D,L-lactide) block copolymer micelles with Modulated Surface Charge," *Journal of Controlled Release.* (2001) 77:27-38.
Zhang et al., "Neointimal Hyperplasia Persists at Six Months after Siroli Mus-Eluting Stent Implantation in Diabetic Porcine," *Cardiovasc. Diabetol.* (2007) 6:16:1-7.
Zhou et al., "NAAG Peptidase Inhibitors and Their Potential for Diagnosis and Therapy," *Nature Rev. Drug Discov.* (2005) 4:1015-1026.

STABLE FORMULATIONS FOR LYOPHILIZING THERAPEUTIC PARTICLES

RELATED APPLICATIONS

This application is a continuation of U.S. application Ser. No. 13/862,090, filed Apr. 12, 2013, which is a continuation of U.S. application Ser. No. 13/664,133, filed Oct. 30, 2012, which is a continuation of U.S. application Ser. No. 12/965,294, filed Dec. 10, 2010, now U.S. Pat. No. 8,357,401, which claims the benefit of and priority to U.S. Provisional Patent Application No. 61/285,722, filed Dec. 11, 2009, each of which is hereby incorporated by reference in its entirety.

BACKGROUND

Systems that deliver certain drugs to a patient (e.g., targeted to a particular tissue or cell type or targeted to a specific diseased tissue but not normal tissue), or that control release of drugs has long been recognized as beneficial.

For example, therapeutics that include an active drug and that are, e.g., targeted to a particular tissue or cell type or targeted to a specific diseased tissue but not to normal tissue, may reduce the amount of the drug in body tissues that do not require treatment. This is particularly important when treating a condition such as cancer where it is desirable that a cytotoxic dose of the drug is delivered to cancer cells without killing the surrounding non-cancerous tissue. Further, such therapeutics may reduce the undesirable and sometimes life-threatening side effects common in anticancer therapy. In addition, such therapeutics may allow drugs to reach certain tissues they would otherwise be unable to reach.

Delivery of therapeutic nanoparticles can be achieved through parenteral injection of a reconstituted suspension of the nanoparticles. The original nanoparticle suspension is lyophilized, i.e., freeze dried, for storage before reconstitution. Freeze drying a nanoparticle suspension potentially creates a product for reconstitution with far superior storage stability than its frozen suspension counterpart. Further, freeze drying may provide easier storage that may not require constant, very low, temperatures. However, the reconstituted lyophilisate must possess physicochemical and performance attributes that are comparable or superior to the original suspension. Redispersing into particles of the same size without trace particulates due to micro-aggregation or undispersed particles is the most challenging aspect of nanoparticle suspension lyophilization.

Accordingly, a need exists for nanoparticle therapeutics and methods of making such nanoparticles, that are capable of delivering therapeutic levels of drug to treat diseases such as cancer, and possess superior storage capabilities.

SUMMARY

In one aspect, the invention provides a lyophilized pharmaceutical composition comprising polymeric nanoparticles, wherein upon reconstitution of the lyophilized pharmaceutical composition, in less than or about 100 mL of an aqueous medium, the reconstituted composition suitable for parenteral administration comprises: less than 6000 microparticles of greater than or equal to 10 microns; and less than 600 microparticles of greater than or equal to 25 microns. In one embodiment, the reconstituted composition comprises less than 3000 microparticles of greater than or equal to 10 microns; and less than 300 microparticles of greater than or equal to 25 microns. In some embodiments, the nanoparticle concentration is about 50 mg/mL.

The number of microparticles can be determined by means such as the USP 32 <788> by light obscuration particle count test, the USP 32 <788> by microscopic particle count test, laser diffraction, and/or single particle optical sensing.

The nanoparticles may include an active agent or therapeutic agent, e.g., taxane, and one, two, or three biocompatible polymers. For example, disclosed herein is a therapeutic nanoparticle comprising about 0.2 to about 35 weight percent of a therapeutic agent; about 10 to about 99 weight percent poly(lactic) acid-block-poly(ethylene)glycol copolymer or poly(lactic)-co-poly(glycolic) acid-block-poly(ethylene) glycol copolymer; and about 0 to about 50 weight percent poly(lactic) acid or poly(lactic) acid-co-poly(glycolic) acid. Exemplary therapeutic agents include antineoplastic agents such as taxanes, e.g., docetaxel and may include about 10 to about 30 weight percent of a therapeutic agent, e.g., a taxane agent.

For example, the poly(lactic) acid portion of the copolymer may have a weight average molecular weight of about 16 kDa and the poly(ethylene)glycol portion of the copolymer may have a weight average molecular weight of about 5 kDa.

Contemplated lyophilized pharmaceutical compositions may further comprise a sugar, e.g. a disaccharide, monosaccharide or polysaccharide, and an ionic halide salt. A disaccharide can be, for example, sucrose or trehalose, or a mixture thereof. The ionic halide salt may be selected from sodium chloride, calcium chloride, and zinc chloride, or mixtures thereof. In other embodiments, the lyophilized pharmaceutical composition may also further comprise a cyclodextrin. For example, the lyophilized pharmaceutical composition may further comprise a sugar such as a disaccharide, an ionic halide salt, and a cyclodextrin. Alternatively, the lyophilized pharmaceutical composition may further comprise a disaccharide and a cyclodextrin, and without the ionic halide salt. The cyclodextrin may be selected from α-cyclodextrin, β-cyclodextrin, γ-cyclodextrin, or mixtures thereof.

The reconstituted composition may have minimal aggregation compared to a reconstituted composition that does not contain an ionic halide salt and/or cyclodextrin. The reconstituted composition may have a polydispersity index of less than 0.2. In some embodiments, the nanoparticles have a concentration of about 10-100 mg/mL, e.g. 40-60 mg/mL, or about 50 mg/mL.

In an aspect, the disclosure provides a pharmaceutical composition suitable for parenteral use upon reconstitution, comprising a plurality of therapeutic particles each comprising a copolymer having a hydrophobic polymer segment and a hydrophilic polymer segment; an active agent; a disaccharide; and an ionic halide salt and/or a cyclodextrin such as a beta-cyclodextrin (e.g. hydroxypropylcyclodextrin (HP-bCD). The pharmaceutical composition may further comprise a cyclodextrin. In another aspect, the disclosure provides a pharmaceutical composition suitable for parenteral use upon reconstitution, comprising a plurality of therapeutic particles each comprising a copolymer having a hydrophobic polymer segment and a hydrophilic polymer segment; an active agent; a disaccharide; and a cyclodextrin.

The ionic halide salt may be selected from the group consisting of sodium chloride, calcium chloride, and zinc chloride, or mixtures thereof. The cyclodextrin may be selected from α-cyclodextrin, β-cyclodextrin, γ-cyclodextrin, or mixtures thereof. For example, the copolymer may be poly(lactic) acid-block-poly(ethylene)glycol copolymer. Upon reconstitution, a 100 mL aqueous sample may comprise less than 6000 particles having a size greater than or equal to 10 microns; and less than 600 particles having a size greater than or equal to 25 microns.

In another aspect, the invention provides a pharmaceutically acceptable formulation for parenteral administration, prepared by a process comprising:

a) providing a composition comprising a plurality of therapeutic particles each comprising a copolymer having a hydrophobic polymer segment and a hydrophilic polymer segment; and an active agent;

b) adding a disaccharide, an ionic halide salt, and optionally a cyclodextrin to said composition;

c) lyophilizing the composition to form a lyophilized composition;

d) reconstituting the lyophilized composition to form the formulation suitable for parenteral administration. The formulation may further comprise a cyclodextrin.

In yet another aspect, the invention provides a pharmaceutically acceptable formulation for parenteral administration, prepared by a process comprising:

a) providing a composition comprising a plurality of therapeutic particles each comprising a copolymer having a hydrophobic polymer segment and a hydrophilic polymer segment; and an active agent;

b) adding a disaccharide and a cyclodextrin to said composition;

c) lyophilizing the composition to form a lyophilized composition;

d) reconstituting the lyophilized composition to form the formulation suitable for parenteral administration.

The lyophilized composition may have a therapeutic particle concentration of greater than about 40 mg/mL. The formulation suitable for parenteral administration may have less than about 600 particles having a size greater than 10 microns in a 10 mL dose.

The step of adding a disaccharide and/or an ionic halide salt may comprise adding about 5 to about 15 weight percent sucrose or about 5 to about 20 weight percent (e.g. about 10 to about 20 weight percent) trehalose and about 10 to about 500 mM ionic halide salt. The step may further comprise adding about 1 to about 25 weight percent cyclodextrin.

In another embodiment, the step of adding a disaccharide and a cyclodextrin may comprise adding about 5 to about 15 weight percent sucrose or about 10 to about 20 weight percent trehalose and about 1 to about 25 weight percent cyclodextrin.

The step of lyophilizing may comprise freezing the composition at a temperature of greater than about −40° C., or a temperature of less than −30° C., e.g. about −40° C. to about −30° C., or about −40° C. to about −25° C. forming a frozen composition; and drying the frozen composition via, e.g., sublimation, to form the lyophilized composition.

In another aspect, the disclosure provides a method of preventing substantial aggregation of particles in a pharmaceutical nanoparticle composition comprising adding a sugar and a salt to the lyophilized formulation to prevent aggregation of the nanoparticles upon reconstitution. In an embodiment, cyclodextrin is also added to the lyophilized formulation. In yet another aspect, the disclosure provides a method of preventing substantial aggregation of particles in a reconstituted pharmaceutical nanoparticle composition comprising adding a sugar and a cyclodextrin to a lyophilized formulation comprising nanoparticles; reconstituting the lyophilized formulation, wherein the reconstituted composition does not have substantial aggregation of the nanoparticles. Also provided herein is a method of preventing substantial aggregation of particles in a pharmaceutical nanoparticle composition comprising adding a sugar and a cyclodextrin to the lyophilized formulation to prevent aggregation of the nanoparticles upon reconstitution.

BRIEF DESCRIPTION OF THE DRAWINGS

FIG. 2A shows particle formation and hardening (upstream processing). FIG. 2B shows particle work up and purification (downstream processing).

DETAILED DESCRIPTION

Figure 1:
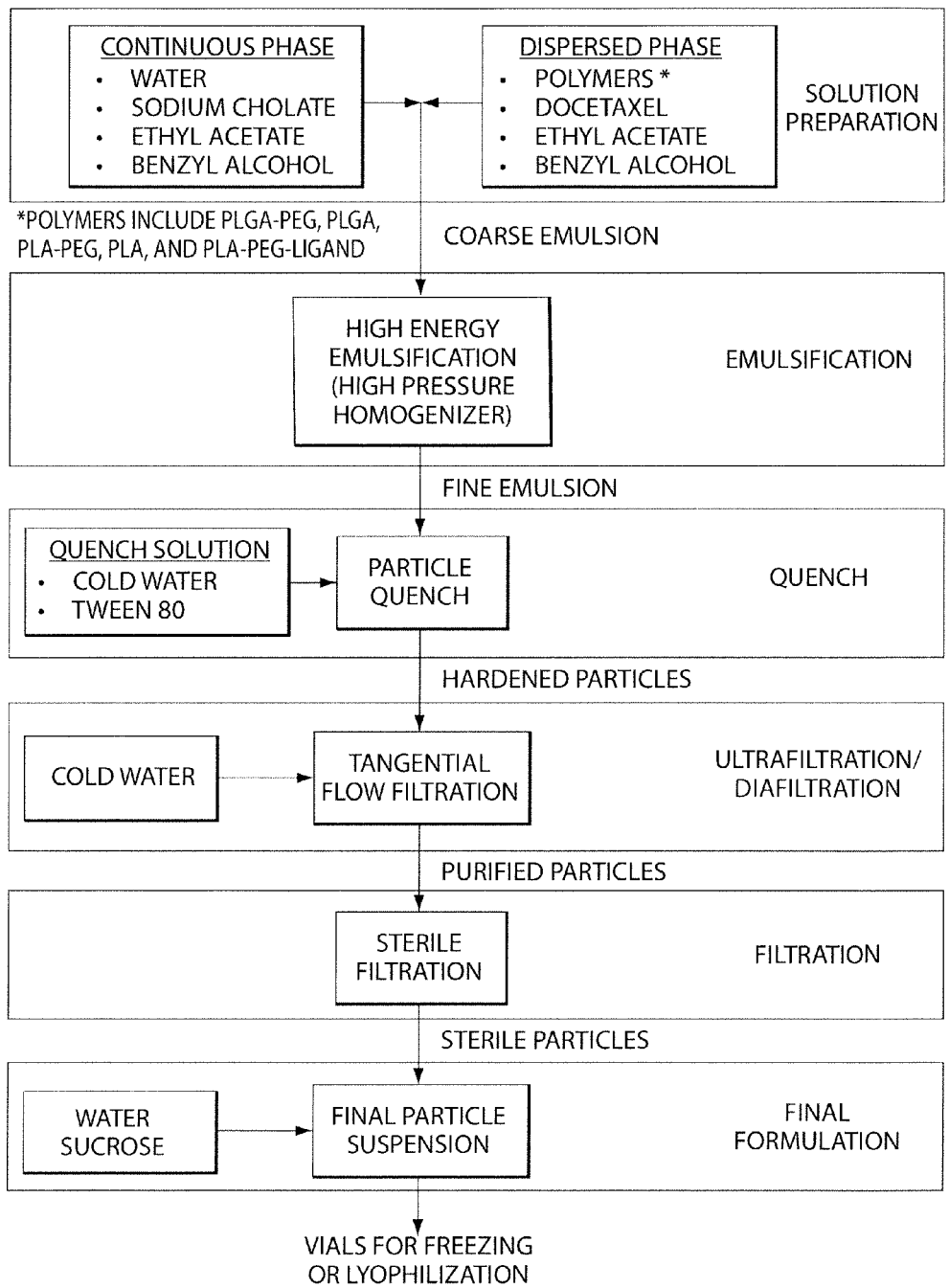
FIG. 1 is a flow chart for an emulsion process for forming disclosed nanoparticles.

The present invention generally relates to lyophilized polymeric nanoparticle compositions, and methods of making and using such therapeutic compositions. Such compositions may be reconstituted from a lyophilized composition, and may include minimal large aggregations of nanoparticles and/or other materials. Disclosed compositions therefore may be suitable for parenteral use.

Nanoparticles

In general, compositions may include nanoparticles that include an active agent. As disclosed herein, "nanoparticle" refers to any particle having a diameter of less than 1000 nm, e.g., about 10 nm to about 200 nm. Disclosed therapeutic nanoparticles may include nanoparticles having a diameter of about 60 nm to about 120 nm, or about 70 nm to about 130 nm, or about 60 nm to about 140 nm.

Disclosed nanoparticles may include about 0.2 to about 35 weight percent, about 3 to about 40 weight percent, about 5 to about 30 weight percent, 10 to about 30 weight percent, 15 to 25 weight percent, or even about 4 to about 25 weight percent of an active agent, such as an antineoplastic agent, e.g., a taxane agent (for example, docetaxel).

Nanoparticles disclosed herein include one, two, three or more biocompatible and/or biodegradable polymers. For example, a contemplated nanoparticle may include about 10 to about 99 weight percent of a one or more block co-polymers that include a biodegradable polymer and polyethylene glycol, and about 0 to about 50 weight percent of a biodegradable homopolymer.

Exemplary therapeutic nanoparticles may include about 40 to about 90 weight percent poly(lactic) acid-poly(ethylene) glycol copolymer or about 40 to about 80 weight percent poly(lactic) acid-poly(ethylene)glycol copolymer. Such poly (lactic) acid-block-poly(ethylene)glycol copolymer may include poly(lactic acid) having a number average molecular weight of about 15 to 20 kDa (or for example about 15 to about 100 kDa, e.g., about 15 to about 80 kDa), and poly (ethylene)glycol having a number average molecular weight of about 2 to about 10 kDa, for example, about 4 to about 6 kDa. For example, a disclosed therapeutic nanoparticle may include about 70 to about 95 weight percent PLA-PEG and about 5 to about 25 weight percent docetaxel. In another example, a disclosed therapeutic nanoparticle may include about 30 to about 50 weight percent PLA-PEG, about 30 to about 50 weight percent PLA or PLGA, and about 5 to about 25 weight percent docetaxel. Such PLA ((poly)lactic acid) may have a number average molecular weight of about 5 to about 10 kDa. Such PLGA (poly lactic-co-glycolic acid) may have a number average molecular weight of about 8 to about 12 kDa.

In one embodiment, disclosed therapeutic nanoparticles may include a targeting ligand, e.g., a low-molecular weight PSMA ligand effective for the treatment of a disease or disorder, such as prostate cancer, in a subject in need thereof. In certain embodiments, the low-molecular weight ligand is conjugated to a polymer, and the nanoparticle comprises a certain ratio of ligand-conjugated polymer (e.g., PLA-PEG-Ligand) to non-functionalized polymer (e.g., PLA-PEG or PLGA-PEG). The nanoparticle can have an optimized ratio of these two polymers such that an effective amount of ligand is associated with the nanoparticle for treatment of a disease or disorder, such as cancer.

In some embodiments, disclosed nanoparticles may further comprise about 0.2 to about 10 weight percent PLA-PEG functionalized with a targeting ligand and/or may include about 0.2 to about 10 weight percent poly(lactic) acid-co poly(glycolic) acid block-PEG-functionalized with a targeting ligand. Such a targeting ligand may be, in some embodiments, covalently bound to the PEG, for example, bound to the PEG via an alkylene linker, e.g., PLA-PEG-alkylene-GL2. For example, a disclosed nanoparticle may include about 0.2 to about 10 mole percent PLA-PEG-GL2 or poly (lactic) acid-co poly(glycolic) acid-PEG-GL2. It is understood that reference to PLA-PEG-GL2 or PLGA-PEG-GL2 refers to moieties that may include an alkylene linker (e.g., $C_1$-$C_{20}$, e.g., $(CH_2)_5$) linking the PEG to GL2.

In an embodiment, a therapeutic nanoparticle may include about 0.2 to about 35 weight percent of a therapeutic agent; about 30 to about 99 weight percent poly(lactic) acid-poly (ethylene)glycol copolymer or poly(lactic)-co-poly(glycolic) acid-poly(ethylene)glycol copolymer; about 0 to about 50 weight percent poly(lactic) acid or poly(lactic) acid-co-poly (glycolic) acid; and about 0.2 to about 10 weight percent, or about 0.2 to about 30 weight percent PLA-PEG-GL2 or poly (lactic) acid-co poly(glycolic) acid-PEG-GL2. For example, PLA-PEG-GL2 may include poly(lactic) acid with a number average molecular weight of about 10,000 Da to about 20,000 Da and poly(ethylene)glycol with a number average molecular weight of about 4,000 to about 8,000.

Polymers

In some embodiments, the nanoparticles of the invention comprise a matrix of polymers and a therapeutic agent. In some embodiments, a therapeutic agent and/or targeting moiety (i.e., a low-molecular weight PSMA ligand) can be associated with at least part of the polymeric matrix. For example, in some embodiments, a targeting moiety (e.g., ligand) can be covalently associated with the surface of a polymeric matrix. In some embodiments, covalent association is mediated by a linker. The therapeutic agent can be associated with the surface of, encapsulated within, surrounded by, and/or dispersed throughout the polymeric matrix.

A wide variety of polymers and methods for forming particles therefrom are known in the art of drug delivery. In some embodiments, the disclosure is directed toward nanoparticles with at least two macromolecules, wherein the first macromolecule comprises a first polymer bound to a low-molecular weight ligand (e.g., targeting moiety); and the second macromolecule comprising a second polymer that is not bound to a targeting moiety. The nanoparticle can optionally include one or more additional, unfunctionalized, polymers.

Any polymer can be used in accordance with the present invention. Polymers can be natural or unnatural (synthetic) polymers. Polymers can be homopolymers or copolymers comprising two or more monomers. In terms of sequence, copolymers can be random, block, or comprise a combination of random and block sequences. Typically, polymers in accordance with the present invention are organic polymers.

The term "polymer," as used herein, is given its ordinary meaning as used in the art, i.e., a molecular structure comprising one or more repeat units (monomers), connected by covalent bonds. The repeat units may all be identical, or in some cases, there may be more than one type of repeat unit present within the polymer. In some cases, the polymer can be biologically derived, i.e., a biopolymer. Non-limiting examples include peptides or proteins. In some cases, additional moieties may also be present in the polymer, for example biological moieties such as those described below. If more than one type of repeat unit is present within the polymer, then the polymer is said to be a "copolymer." It is to be understood that in any embodiment employing a polymer, the polymer being employed may be a copolymer in some cases. The repeating units forming the copolymer may be arranged in any fashion. For example, the repeating units may be arranged in a random order, in an alternating order, or as a block copolymer, i.e., comprising one or more regions each comprising a first repeat unit (e.g., a first block), and one or more regions each comprising a second repeat unit (e.g., a second block), etc. Block copolymers may have two (a diblock copolymer), three (a triblock copolymer), or more numbers of distinct blocks.

Disclosed particles can include copolymers, which, in some embodiments, describes two or more polymers (such as those described herein) that have been associated with each other, usually by covalent bonding of the two or more polymers together. Thus, a copolymer may comprise a first polymer and a second polymer, which have been conjugated together to form a block copolymer where the first polymer can be a first block of the block copolymer and the second polymer can be a second block of the block copolymer. Of course, those of ordinary skill in the art will understand that a block copolymer may, in some cases, contain multiple blocks of polymer, and that a "block copolymer," as used herein, is not limited to only block copolymers having only a single first block and a single second block. For instance, a block copolymer may comprise a first block comprising a first polymer, a second block comprising a second polymer, and a third block comprising a third polymer or the first polymer, etc. In some cases, block copolymers can contain any number of first blocks of a first polymer and second blocks of a second polymer (and in certain cases, third blocks, fourth blocks, etc.). In addition, it should be noted that block copolymers can also be formed, in some instances, from other block copolymers. For example, a first block copolymer may be conjugated to another polymer (which may be a homopolymer, a biopolymer, another block copolymer, etc.), to form a new block copolymer containing multiple types of blocks, and/or to other moieties (e.g., to non-polymeric moieties).

In some embodiments, the polymer (e.g., copolymer, e.g., block copolymer) can be amphiphilic, i.e., having a hydrophilic portion and a hydrophobic portion, or a relatively hydrophilic portion and a relatively hydrophobic portion. A hydrophilic polymer can be one generally that attracts water and a hydrophobic polymer can be one that generally repels water. A hydrophilic or a hydrophobic polymer can be identified, for example, by preparing a sample of the polymer and measuring its contact angle with water (typically, the polymer will have a contact angle of less than 60°, while a hydrophobic polymer will have a contact angle of greater than about 60°). In some cases, the hydrophilicity of two or more polymers may be measured relative to each other, i.e., a first polymer may be more hydrophilic than a second polymer. For instance, the first polymer may have a smaller contact angle than the second polymer.

In one set of embodiments, a polymer (e.g., copolymer, e.g., block copolymer) contemplated herein includes a biocompatible polymer, i.e., the polymer that does not typically induce an adverse response when inserted or injected into a living subject, for example, without significant inflammation and/or acute rejection of the polymer by the immune system, for instance, via a T-cell response. Accordingly, the therapeutic particles contemplated herein can be non-immunogenic. The term non-immunogenic as used herein refers to endogenous growth factor in its native state which normally elicits no, or only minimal levels of, circulating antibodies, T-cells, or reactive immune cells, and which normally does not elicit in the individual an immune response against itself.

Biocompatibility typically refers to the acute rejection of material by at least a portion of the immune system, i.e., a nonbiocompatible material implanted into a subject provokes an immune response in the subject that can be severe enough such that the rejection of the material by the immune system cannot be adequately controlled, and often is of a degree such that the material must be removed from the subject. One simple test to determine biocompatibility can be to expose a polymer to cells in vitro; biocompatible polymers are polymers that typically will not result in significant cell death at moderate concentrations, e.g., at concentrations of 50 micrograms/$10^6$ cells. For instance, a biocompatible polymer may cause less than about 20% cell death when exposed to cells such as fibroblasts or epithelial cells, even if phagocytosed or otherwise uptaken by such cells. Non-limiting examples of biocompatible polymers that may be useful in various embodiments of the present invention include polydioxanone (PDO), polyhydroxyalkanoate, polyhydroxybutyrate, poly (glycerol sebacate), polyglycolide, polylactide, PLGA, polycaprolactone, or copolymers or derivatives including these and/or other polymers.

In certain embodiments, contemplated biocompatible polymers may be biodegradable, i.e., the polymer is able to degrade, chemically and/or biologically, within a physiological environment, such as within the body. As used herein, "biodegradable" polymers are those that, when introduced into cells, are broken down by the cellular machinery (biologically degradable) and/or by a chemical process, such as hydrolysis, (chemically degradable) into components that the cells can either reuse or dispose of without significant toxic effect on the cells. In one embodiment, the biodegradable polymer and their degradation byproducts can be biocompatible.

For instance, a contemplated polymer may be one that hydrolyzes spontaneously upon exposure to water (e.g., within a subject), the polymer may degrade upon exposure to heat (e.g., at temperatures of about 37° C.). Degradation of a polymer may occur at varying rates, depending on the polymer or copolymer used. For example, the half-life of the polymer (the time at which 50% of the polymer can be degraded into monomers and/or other nonpolymeric moieties) may be on the order of days, weeks, months, or years, depending on the polymer. The polymers may be biologically degraded, e.g., by enzymatic activity or cellular machinery, in some cases, for example, through exposure to a lysozyme (e.g., having relatively low pH). In some cases, the polymers may be broken down into monomers and/or other nonpolymeric moieties that cells can either reuse or dispose of without significant toxic effect on the cells (for example, polylactide may be hydrolyzed to form lactic acid, polyglycolide may be hydrolyzed to form glycolic acid, etc.).

In some embodiments, polymers may be polyesters, including copolymers comprising lactic acid and glycolic acid units, such as poly(lactic acid-co-glycolic acid) and poly (lactide-co-glycolide), collectively referred to herein as "PLGA"; and homopolymers comprising glycolic acid units, referred to herein as "PGA," and lactic acid units, such as poly-L-lactic acid, poly-D-lactic acid, poly-D,L-lactic acid, poly-L-lactide, poly-D-lactide, and poly-D,L-lactide, collectively referred to herein as "PLA." In some embodiments, exemplary polyesters include, for example, polyhydroxyacids; PEGylated polymers and copolymers of lactide and glycolide (e.g., PEGylated PLA, PEGylated PGA, PEGylated PLGA, and derivatives thereof. In some embodiments, polyesters include, for example, polyanhydrides, poly(ortho ester) PEGylated poly(ortho ester), poly(caprolactone), PEGylated poly(caprolactone), polylysine, PEGylated polylysine, poly(ethylene imine), PEGylated poly(ethylene imine), poly(L-lactide-co-L-lysine), poly(serine ester), poly (4-hydroxy-L-proline ester), poly[α-(4-aminobutyl)-L-glycolic acid], and derivatives thereof.

In some embodiments, a polymer may be PLGA. PLGA is a biocompatible and biodegradable co-polymer of lactic acid and glycolic acid, and various forms of PLGA can be characterized by the ratio of lactic acid:glycolic acid. Lactic acid can be L-lactic acid, D-lactic acid, or D,L-lactic acid. The degradation rate of PLGA can be adjusted by altering the lactic acid-glycolic acid ratio. In some embodiments, PLGA to be used in accordance with the present invention can be characterized by a lactic acid:glycolic acid ratio of approximately 85:15, approximately 75:25, approximately 60:40, approximately 50:50, approximately 40:60, approximately 25:75, or approximately 15:85. In some embodiments, the ratio of lactic acid to glycolic acid monomers in the polymer of the particle (e.g., the PLGA block copolymer or PLGA-PEG block copolymer), may be selected to optimize for various parameters such as water uptake, therapeutic agent release and/or polymer degradation kinetics can be optimized.

In some embodiments, polymers may be one or more acrylic polymers. In certain embodiments, acrylic polymers include, for example, acrylic acid and methacrylic acid copolymers, methyl methacrylate copolymers, ethoxyethyl methacrylates, cyanoethyl methacrylate, amino alkyl methacrylate copolymer, poly(acrylic acid), poly(methacrylic acid), methacrylic acid alkylamide copolymer, poly(methyl methacrylate), poly(methacrylic acid polyacrylamide, amino alkyl methacrylate copolymer, glycidyl methacrylate copolymers, polycyanoacrylates, and combinations comprising one or more of the foregoing polymers. The acrylic polymer may comprise fully-polymerized copolymers of acrylic and methacrylic acid esters with a low content of quaternary ammonium groups.

In some embodiments, polymers can be cationic polymers. In general, cationic polymers are able to condense and/or protect negatively charged strands of nucleic acids (e.g. DNA, RNA, or derivatives thereof). Amine-containing polymers such as poly(lysine), polyethylene imine (PEI), and poly(amidoamine) dendrimers are contemplated for use, in some embodiments, in a disclosed particle.

In some embodiments, polymers can be degradable polyesters bearing cationic side chains. Examples of these polyesters include poly(L-lactide-co-L-lysine), poly(serine ester), poly(4-hydroxy-L-proline ester).

Particles disclosed herein may or may not contain PEG. In addition, certain embodiments can be directed towards copolymers containing poly(ester-ether)s, e.g., polymers having repeat units joined by ester bonds (e.g., R—C(O)—O—R' bonds) and ether bonds (e.g., R—O—R' bonds). In some embodiments of the invention, a biodegradable polymer, such as a hydrolyzable polymer, containing carboxylic acid groups, may be conjugated with poly(ethylene glycol) repeat units to form a poly(ester-ether). A polymer (e.g., copolymer, e.g., block copolymer) containing poly(ethylene glycol) repeat units can also be referred to as a "PEGylated" polymer.

It is contemplated that PEG may be terminated and include an end group, for example, when PEG is not conjugated to a ligand. For example, PEG may terminate in a hydroxyl, a methoxy or other alkoxyl group, a methyl or other alkyl group, an aryl group, a carboxylic acid, an amine, an amide, an acetyl group, a guanidino group, or an imidazole. Other contemplated end groups include azide, alkyne, maleimide, aldehyde, hydrazide, hydroxylamine, alkoxyamine, or thiol moieties.

Those of ordinary skill in the art will know of methods and techniques for PEGylating a polymer, for example, by using EDC (1-ethyl-3-(3-dimethylaminopropyl) carbodiimide hydrochloride) and NHS(N-hydroxysuccinimide) to react a polymer to a PEG group terminating in an amine, by ring opening polymerization techniques (ROMP), or the like In one embodiment, the molecular weight of the polymers can be optimized for effective treatment as disclosed herein. For example, the molecular weight of a polymer may influence particle degradation rate (such as when the molecular weight of a biodegradable polymer can be adjusted), solubility, water uptake, and drug release kinetics. For example, the molecular weight of the polymer can be adjusted such that the particle biodegrades in the subject being treated within a reasonable period of time (ranging from a few hours to 1-2 weeks, 3-4 weeks, 5-6 weeks, 7-8 weeks, etc.). A disclosed particle can for example comprise a diblock copolymer of PEG and PL(G)A, wherein for example, the PEG portion may have a number average molecular weight of about 1,000-20,000, e.g., about 2,000-20,000, e.g., about 2 to about 10,000, and the PL(G)A portion may have a number average molecular weight of about 5,000 to about 20,000, or about 5,000-100,000, e.g., about 20,000-70,000, e.g., about 15,000-50,000.

For example, disclosed here is an exemplary therapeutic nanoparticle that includes about 10 to about 99 weight percent poly(lactic) acid-poly(ethylene)glycol copolymer or poly(lactic)-co-poly(glycolic) acid-poly(ethylene)glycol copolymer, or about 20 to about 80 weight percent, about 40 to about 80 weight percent, or about 30 to about 50 weight percent, or about 70 to about 90 weight percent poly(lactic) acid-poly(ethylene)glycol copolymer or poly(lactic)-co-poly(glycolic) acid-poly(ethylene)glycol copolymer. Exemplary poly(lactic) acid-poly(ethylene)glycol copolymers can include a number average molecular weight of about 15 to about 20 kDa, or about 10 to about 25 kDa of poly(lactic) acid and a number average molecular weight of about 4 to about 6, or about 2 kDa to about 10 kDa of poly(ethylene)glycol.

Disclosed nanoparticles may optionally include about 1 to about 50 weight percent poly(lactic) acid or poly(lactic) acid-co-poly(glycolic) acid (which does not include PEG), or may optionally include about 1 to about 50 weight percent, or about 10 to about 50 weight percent or about 30 to about 50 weight percent poly(lactic) acid or poly(lactic) acid-co-poly(glycolic) acid. For example, poly(lactic) or poly(lactic)-co-poly(glycolic) acid may have a number average molecule weight of about 5 to about 15 kDa, or about 5 to about 12 kDa. Exemplary PLA may have a number average molecular weight of about 5 to about 10 kDa. Exemplary PLGA may have a number average molecular weight of about 8 to about 12 kDa.

In certain embodiments, the polymers of the nanoparticles can be conjugated to a lipid. The polymer can be, for example, a lipid-terminated PEG. As described below, the lipid portion of the polymer can be used for self assembly with another polymer, facilitating the formation of a nanoparticle. For example, a hydrophilic polymer could be conjugated to a lipid that will self assemble with a hydrophobic polymer.

In some embodiments, lipids are oils. In general, any oil known in the art can be conjugated to the polymers used in the invention. In some embodiments, an oil can comprise one or more fatty acid groups or salts thereof. In some embodiments, a fatty acid group can comprise digestible, long chain (e.g., $C_8$-$C_{50}$), substituted or unsubstituted hydrocarbons. In some embodiments, a fatty acid group can be a $C_{10}$-$C_{20}$ fatty acid or salt thereof. In some embodiments, a fatty acid group can be a $C_{15}$-$C_{20}$ fatty acid or salt thereof. In some embodiments, a fatty acid can be unsaturated. In some embodiments, a fatty acid group can be monounsaturated. In some embodiments, a fatty acid group can be polyunsaturated. In some embodiments, a double bond of an unsaturated fatty acid group can be in the cis conformation. In some embodiments, a double bond of an unsaturated fatty acid can be in the trans conformation.

In some embodiments, a fatty acid group can be one or more of butyric, caproic, caprylic, capric, lauric, myristic, palmitic, stearic, arachidic, behenic, or lignoceric acid. In some embodiments, a fatty acid group can be one or more of palmitoleic, oleic, vaccenic, linoleic, alpha-linolenic, gamma-linoleic, arachidonic, gadoleic, arachidonic, eicosapentaenoic, docosahexaenoic, or erucic acid.

In one embodiment, optional small molecule targeting moieties are bonded, e.g., covalently bonded, to the lipid component of the nanoparticle. For example, provided herein is a nanoparticle comprising a therapeutic agent, a polymeric matrix comprising functionalized and non-functionalized polymers, a lipid, and a low-molecular weight PSMA targeting ligand, wherein the targeting ligand is bonded, e.g., covalently bonded, to the lipid component of the nanoparticle. In one embodiment, the lipid component that is bonded to the low-molecular weight targeting moiety is of the Formula V:

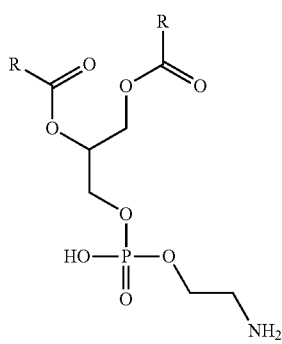

and salts thereof, wherein each R is, independently, $C_{1-30}$ alkyl. In one embodiment of Formula V, the lipid can be 1,2 distearoyl-sn-glycero-3-phosphoethanolamine (DSPE), and salts thereof, e.g., the sodium salt. In another embodiment, the invention provides a target-specific nanoparticle comprising a therapeutic agent, a polymeric matrix, DSPE, and a low-molecular weight PSMA targeting ligand, wherein the ligand is bonded, e.g., covalently bonded, to DSPE. For example, the nanoparticle of the invention may comprise a polymeric matrix comprising PLGA-DSPE-PEG-Ligand.

A contemplated nanoparticle may include a ratio of ligand-bound polymer to non-functionalized polymer effective for the treatment of prostate cancer, wherein the hydrophilic, ligand-bound polymer is conjugated to a lipid that will self assemble with the hydrophobic polymer, such that the hydrophobic and hydrophilic polymers that constitute the nanoparticle are not covalently bound. "Self-assembly" refers to a process of spontaneous assembly of a higher order structure that relies on the natural attraction of the components of the higher order structure (e.g., molecules) for each other. It typically occurs through random movements of the molecules and formation of bonds based on size, shape, composition, or chemical properties. For example, such a method comprises providing a first polymer that is reacted with a lipid, to form a polymer/lipid conjugate. The polymer/lipid conjugate is then reacted with the low-molecular weight ligand to prepare a ligand-bound polymer/lipid conjugate; and mixing the ligand-bound polymer/lipid conjugate with a second, non-functionalized polymer, and the therapeutic agent; such that the nanoparticle is formed. In certain embodiments, the first polymer is PEG, such that a lipid-terminated PEG is formed. In one embodiment, the lipid is of the Formula V, e.g., 2 distearoyl-sn-glycero-3-phosphoethanolamine (DSPE), and salts thereof, e.g., the sodium salt. The lipid-terminated PEG can then, for example, be mixed with PLGA to form a nanoparticle.

Targeting Moieties

Provided herein are nanoparticles that may include an optional targeting moiety, i.e., a moiety able to bind to or otherwise associate with a biological entity, for example, a membrane component, a cell surface receptor, prostate specific membrane antigen, or the like. A targeting moiety present on the surface of the particle may allow the particle to become localized at a particular targeting site, for instance, a tumor, a disease site, a tissue, an organ, a type of cell, etc. As such, the nanoparticle may then be "target specific." The drug or other payload may then, in some cases, be released from the particle and allowed to interact locally with the particular targeting site.

In a particular embodiment, the drug or other payload may be released in a controlled release manner from the particle and allowed to interact locally with the particular targeting site (e.g., a tumor). The term "controlled release" (and variants of that term) as used herein (e.g., in the context of "controlled-release system") is generally meant to encompass release of a substance (e.g., a drug) at a selected site or otherwise controllable in rate, interval, and/or amount. Controlled release encompasses, but is not necessarily limited to, substantially continuous delivery, patterned delivery (e.g., intermittent delivery over a period of time that is interrupted by regular or irregular time intervals), and delivery of a bolus of a selected substance (e.g., as a predetermined, discrete amount if a substance over a relatively short period of time (e.g., a few seconds or minutes)).

In one embodiment, a disclosed nanoparticle includes a targeting moiety that is a low-molecular weight ligand, e.g., a low-molecular weight PSMA ligand. The term "bind" or "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Biological binding" defines a type of interaction that occurs between pairs of molecules including proteins, nucleic acids, glycoproteins, carbohydrates, hormones, or the like. The term "binding partner" refers to a molecule that can undergo binding with a particular molecule. "Specific binding" refers to molecules, such as polynucleotides, that are able to bind to or recognize a binding partner (or a limited number of binding partners) to a substantially higher degree than to other, similar biological entities. In one set of embodiments, the targeting moiety has an affinity (as measured via a disassociation constant) of less than about 1 micromolar, at least about 10 micromolar, or at least about 100 micromolar.

For example, a targeting portion may cause the particles to become localized to a tumor (e.g., a solid tumor) a disease site, a tissue, an organ, a type of cell, etc. within the body of a subject, depending on the targeting moiety used. For example, a low-molecular weight PSMA ligand may become localized to a solid tumor, e.g., breast or prostate tumors or cancer cells. The subject may be a human or non-human animal. Examples of subjects include, but are not limited to, a mammal such as a dog, a cat, a horse, a donkey, a rabbit, a cow, a pig, a sheep, a goat, a rat, a mouse, a guinea pig, a hamster, a primate, a human or the like.

For example, a targeting moiety may small target prostate cancer tumors, for example a target moiety may be PSMA peptidase inhibitor. These moieties are also referred to herein as "low-molecular weight PSMA ligands." When compared with expression in normal tissues, expression of prostate specific membrane antigen (PSMA) is at least 10-fold overexpressed in malignant prostate relative to normal tissue, and the level of PSMA expression is further up-regulated as the disease progresses into metastatic phases (Silver et al. 1997, *Clin. Cancer Res.*, 3:81).

For example, the low-molecular weight PSMA ligand is

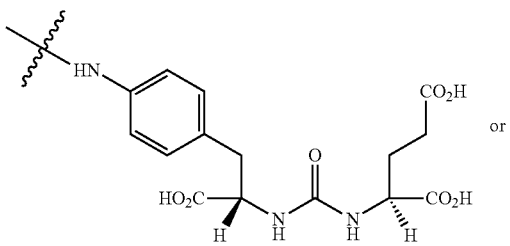

-continued

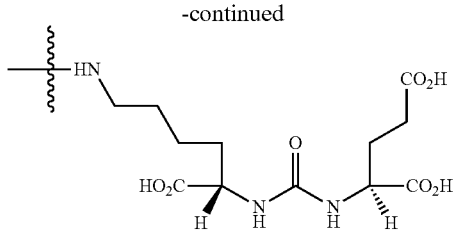

and enantiomers, stereoisomers, rotamers, tautomers, diastereomers, or racemates thereof. Particularly, the butyl-amine compound has the advantage of ease of synthesis, especially because of its lack of a benzene ring.

For example, a disclosed nanoparticle may include a conjugate represented by:

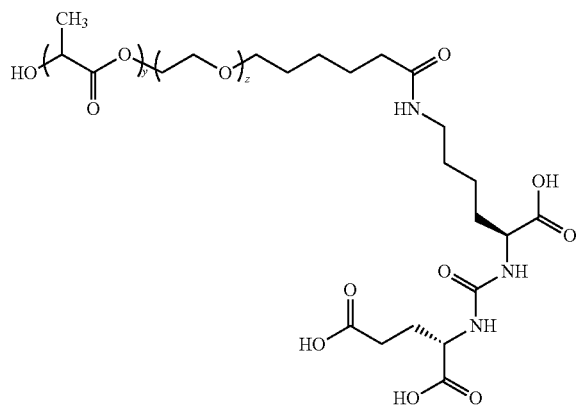

where y is about 222 and z is about 114.

For example, a disclosed nanoparticle includes a polymeric compound selected from:

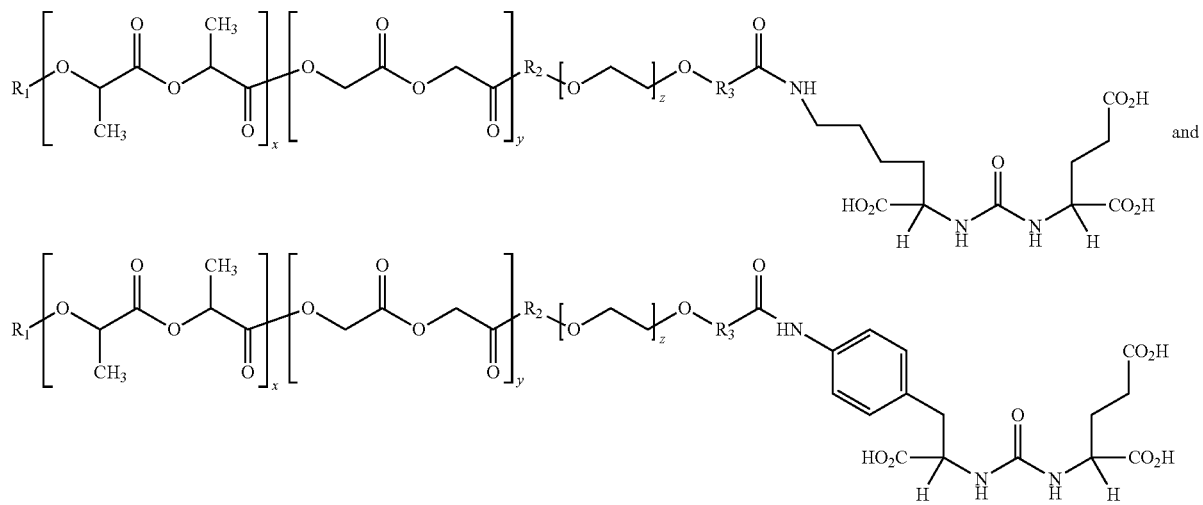

wherein $R_1$ is selected from the group consisting of H, and a $C_1$-$C_{20}$ alkyl group optionally substituted with halogen;

$R_2$ is a bond, an ester linkage, or amide linkage;

$R_3$ is an $C_1$-$C_{10}$ alkylene or a bond;

x is 50 to about 1500, for example about 170 to about 260;

y is 0 to about 50, for example y is 0; and z is about 30 to about 456, or about 30 to about 200, for example, z is about 80 to about 130.

Therapeutic Agents

Agents including, for example, therapeutic agents (e.g., anti-cancer agents), diagnostic agents (e.g., contrast agents; radionuclides; and fluorescent, luminescent, and magnetic moieties), prophylactic agents (e.g., vaccines), and/or nutraceutical agents (e.g., vitamins, minerals, etc.) compose part of the disclosed nanoparticles. Exemplary agents to be delivered in accordance with the present invention include, but are not limited to, small molecules (e.g., cytotoxic agents), nucleic acids (e.g., siRNA, RNAi, and microRNA agents), proteins (e.g., antibodies), peptides, lipids, carbohydrates, hormones, metals, radioactive elements and compounds, drugs, vaccines, immunological agents, etc., and/or combinations thereof. In some embodiments, the agent to be delivered is an agent useful in the treatment of cancer (e.g., prostate cancer).

The active agent or drug may be a therapeutic agent (e.g. a chemotherapeutic) such as mTor inhibitors (e.g., sirolimus, temsirolimus, or everolimus), vinca alkaloids (e.g. vinorelbine or vincristine), a diterpene derivative, a taxane (e.g. paclitaxel or its derivatives such as DHA-paclitaxel or PG-paclitaxel, or docetaxel),), a cardiovascular agent (e.g. a diuretic, a vasodilator, angiotensin converting enzyme, a beta blocker, an aldosterone antagonist, or a blood thinner), a corticosteroid, an antimetabolite or antifolate agent (e.g. methotrexate), a chemotherapeutic agent (e.g. epothilone B), an alkylating agent (e.g. bendamustine), or the active agent or drug may be an siRNA.

In an embodiment, an active or therapeutic agent may (or may not be) conjugated to e.g. a disclosed polymer that forms part of a disclosed nanoparticle, e.g an active agent may be conjugated (e.g. covalently bound, e.g. directly or through a linking moiety) to PLA or PGLA, or a PLA or PLGA portion of a copolymer such as PLA-PEG or PLGA-PEG Preparation of Nanoparticles Another aspect of this disclosure is directed to systems and methods of making disclosed nanoparticles. In some embodiments, using two or more different polymers (e.g., copolymers, e.g., block copolymers) in different ratios and producing particles from the polymers (e.g., copolymers, e.g., block copolymers), properties of the particles be controlled. For example, one polymer (e.g., copolymer, e.g., block copolymer) may include a low-molecular weight PSMA ligand, while another polymer (e.g., copolymer, e.g., block copolymer) may be chosen for its biocompatibility and/or its ability to control immunogenicity of the resultant particle.

In one set of embodiments, the particles are formed by providing a solution comprising one or more polymers, and contacting the solution with a polymer nonsolvent to produce the particle. The solution may be miscible or immiscible with the polymer nonsolvent. For example, a water-miscible liquid such as acetonitrile may contain the polymers, and particles are formed as the acetonitrile is contacted with water, a polymer nonsolvent, e.g., by pouring the acetonitrile into the water at a controlled rate. The polymer contained within the solution, upon contact with the polymer nonsolvent, may then precipitate to form particles such as nanoparticles. Two liquids are said to be "immiscible" or not miscible, with each other when one is not soluble in the other to a level of at least 10% by weight at ambient temperature and pressure. Typically, an organic solution (e.g., dichloromethane, acetonitrile, chloroform, tetrahydrofuran, acetone, formamide, dimethylformamide, pyridines, dioxane, dimethysulfoxide, etc.) and an aqueous liquid (e.g., water, or water containing dissolved salts or other species, cell or biological media, ethanol, etc.) are immiscible with respect to each other. For example, the first solution may be poured into the second solution (at a suitable rate or speed). In some cases, particles such as nanoparticles may be formed as the first solution contacts the immiscible second liquid, e.g., precipitation of the polymer upon contact causes the polymer to form nanoparticles while the first solution is poured into the second liquid, and in some cases, for example, when the rate of introduction is carefully controlled and kept at a relatively slow rate, nanoparticles may form. The control of such particle formation can be readily optimized by one of ordinary skill in the art using only routine experimentation.

Figure 2A:
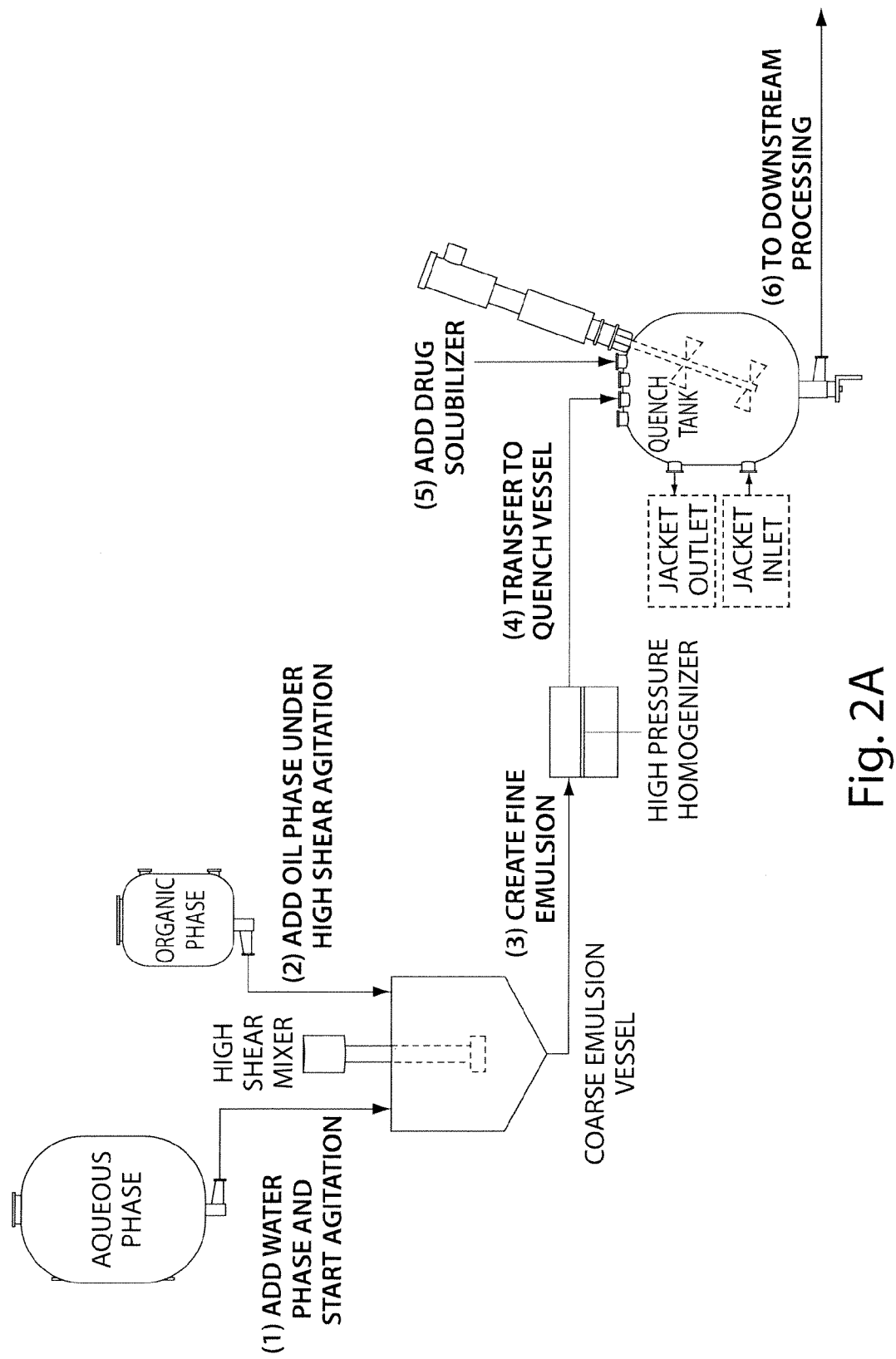
FIGS. 2A and 2B are flow diagrams for a disclosed emulsion process.
Figure 2B:
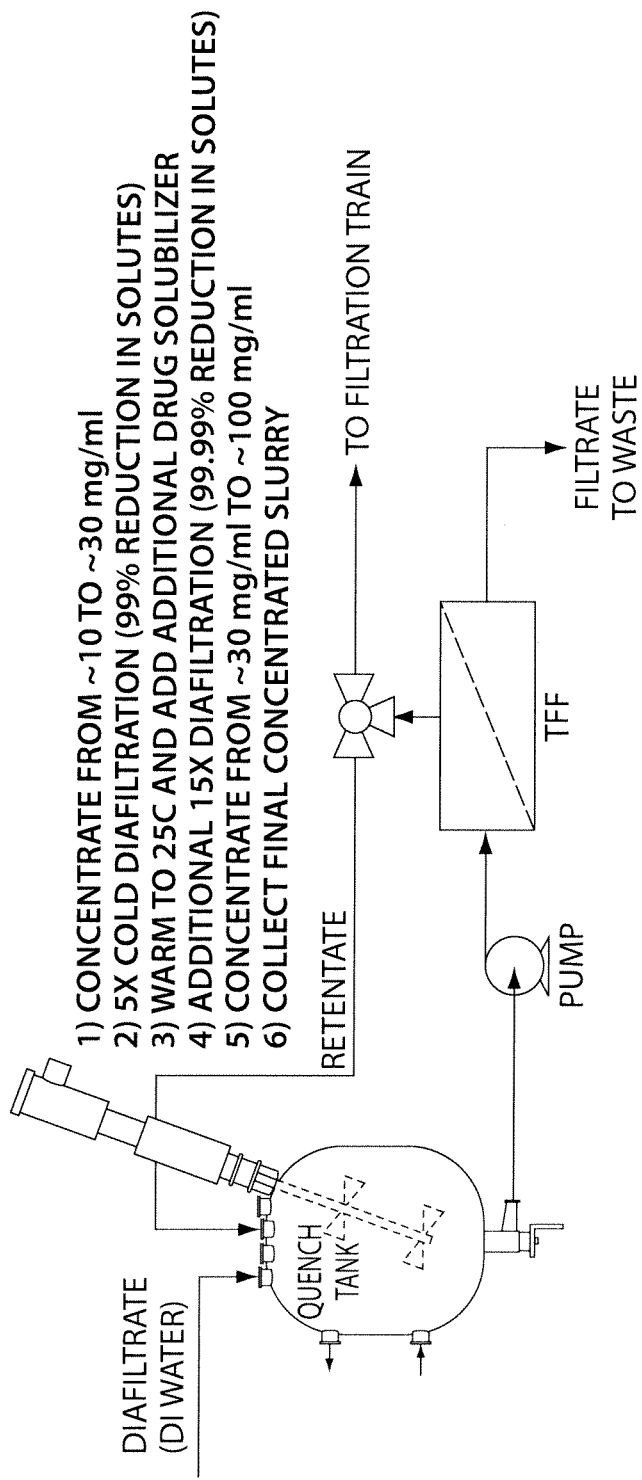

In another embodiment, a nanoemulsion process is provided, such as the process represented in FIGS. 1, 2A, and 2B. For example, a therapeutic agent, a first polymer (for example, a diblock co-polymer such as PLA-PEG or PLGA-PEG, either of which may be optionally bound to a ligand, e.g., GL2) and an optional second polymer (e.g., (PL(G)A-PEG or PLA), with an organic solution to form a first organic phase. Such first phase may include about 5 to about 50% weight solids, e.g about 5 to about 40% solids, or about 10 to about 30% solids. The first organic phase may be combined with a first aqueous solution to form a second phase. The organic solution can include, for example, toluene, methyl ethyl ketone, acetonitrile, tetrahydrofuran, ethyl acetate, isopropyl alcohol, isopropyl acetate, dimethylformamide, methylene chloride, dichloromethane, chloroform, acetone, benzyl alcohol, Tween 80, Span 80, or the like, and combinations thereof. In an embodiment, the organic phase may include benzyl alcohol, ethyl acetate, and combinations thereof. The second phase can be between about 1 and 50 weight percent, e.g., about 5-40 weight percent, solids. The aqueous solution can be water, optionally in combination with one or more of sodium cholate, ethyl acetate, polyvinyl acetate and benzyl alcohol.

For example, the oil or organic phase may use solvent that is only partially miscible with the nonsolvent (water). Therefore, when mixed at a low enough ratio and/or when using water pre-saturated with the organic solvents, the oil phase remains liquid. The oil phase may be emulsified into an aqueous solution and, as liquid droplets, sheared into nanoparticles using, for example, high energy dispersion systems, such as homogenizers or sonicators. The aqueous portion of the emulsion, otherwise known as the "water phase", may be a surfactant solution consisting of sodium cholate and pre-saturated with ethyl acetate and benzyl alcohol.

Emulsifying the second phase to form an emulsion phase may be performed in one or two emulsification steps. For example, a primary emulsion may be prepared, and then emulsified to form a fine emulsion. The primary emulsion can be formed, for example, using simple mixing, a high pressure homogenizer, probe sonicator, stir bar, or a rotor stator homogenizer. The primary emulsion may be formed into a fine emulsion through the use of e.g., probe sonicator or a high pressure homogenizer, e.g., by using 1, 2, 3 or more passes through a homogenizer. For example, when a high pressure homogenizer is used, the pressure used may be about 1000 to about 8000 psi, about 2000 to about 4000 psi 4000 to about 8000 psi, or about 4000 to about 5000 psi, e.g., about 2000, 2500, 4000 or 5000 psi.

Either solvent evaporation or dilution may be needed to complete the extraction of the solvent and solidify the particles. For better control over the kinetics of extraction and a more scalable process, a solvent dilution via aqueous quench may be used. For example, the emulsion can be diluted into cold water to a concentration sufficient to dissolve all of the organic solvent to form a quenched phase. Quenching may be performed at least partially at a temperature of about 5° C. or less. For example, water used in the quenching may be at a temperature that is less that room temperature (e.g., about 0 to about 10° C., or about 0 to about 5° C.).

In some embodiments, not all of the therapeutic agent (e.g., docetaxel) is encapsulated in the particles at this stage, and a drug solubilizer is added to the quenched phase to form a solubilized phase. The drug solubilizer may be for example, Tween 80, Tween 20, polyvinyl pyrrolidone, cyclodextran, sodium dodecyl sulfate, or sodium cholate. For example, Tween-80 may added to the quenched nanoparticle suspension to solubilize the free drug and prevent the formation of drug crystals. In some embodiments, a ratio of drug solubilizer to therapeutic agent (e.g., docetaxel) is about 100:1 to about 10:1.

The solubilized phase may be filtered to recover the nanoparticles. For example, ultrafiltration membranes may be used to concentrate the nanoparticle suspension and substantially eliminate organic solvent, free drug, and other processing aids (surfactants). Exemplary filtration may be performed using a tangential flow filtration system. For example, by using a membrane with a pore size suitable to retain nanoparticles while allowing solutes, micelles, and organic solvent to pass, nanoparticles can be selectively separated. Exemplary membranes with molecular weight cut-offs of about 300-500 kDa (~5-25 nm) may be used.

Diafiltration may be performed using a constant volume approach, meaning the diafiltrate (cold deionized water, e.g., about 0 to about 5° C., or 0 to about 10° C.) may added to the feed suspension at the same rate as the filtrate is removed from the suspension. In some embodiments, filtering may include a first filtering using a first temperature of about 0 to about 5° C., or 0 to about 10° C., and a second temperature of about 20 to about 30° C., or 15 to about 35° C. For example, filtering may include processing about 1 to about 6 diavolumes at about 0 to about 5° C., and processing at least one diavolume (e.g., about 1 to about 3 or about 1-2 diavolumes) at about 20 to about 30° C.

After purifying and concentrating the nanoparticle suspension, the particles may be passed through one, two or more sterilizing and/or depth filters, for example, using ~0.2 μm depth pre-filter.

In another embodiment of preparing nanoparticles, an organic phase is formed composed of a mixture of a therapeutic agent, e.g., docetaxel, and polymer (homopolymer, co-polymer, and co-polymer with ligand). The organic phase is mixed with an aqueous phase at approximately a 1:5 ratio (oil phase:aqueous phase) where the aqueous phase is composed of a surfactant and some dissolved solvent. The primary emulsion is formed by the combination of the two phases under simple mixing or through the use of a rotor stator homogenizer. The primary emulsion is then formed into a fine emulsion through the use of a high pressure homogenizer. The fine emulsion is then quenched by addition to deionized water under mixing. The quench:emulsion ratio is approximately 8.5:1. Then a solution of Tween (e.g., Tween 80) is added to the quench to achieve approximately 2% Tween overall. This serves to dissolve free, unencapsulated drug. The nanoparticles are then isolated through either centrifugation or ultrafiltration/diafiltration.

It will be appreciated that the amounts of polymer and therapeutic or active agent that are used in the preparation of the formulation may differ from a final formulation. For example, some active agent may not become completely incorporated into a nanoparticle and such free therapeutic agent may be e.g., filtered away. For example, in an embodiment, about 20 weight percent of active agent (e.g., docetaxel) and about 80 weight percent polymer (e.g., the polymer may include about 2.5 mol percent PLA-PEG-GL2 and about 97.5 mol percent PLA-PEG). may be used in the preparation of a formulation that results in an e.g., final nanoparticle comprising about 10 weight percent active agent (e.g., docetaxel) and about 90 weight percent polymer (where the polymer may include about 1.25 mol percent PLA-PEG-GL2 and about 98.75 mol percent PLA-PEG). Such processes may provide final nanoparticles suitable for administration to a patient that includes about 2 to about 20 percent by weight therapeutic agent, e.g., about 5, about 8, about 10, about 15 percent therapeutic agent by weight.

Lyophilized Pharmaceutical Compositions

Nanoparticles disclosed herein may be combined with pharmaceutical acceptable carriers to form a pharmaceutical composition, according to another aspect of the invention. As would be appreciated by one of skill in this art, the carriers may be chosen based on the route of administration as described below, the location of the target issue, the drug being delivered, the time course of delivery of the drug, etc.

The pharmaceutical compositions of this invention can be administered to a patient by any means known in the art including oral and parenteral routes. The term "patient," as used herein, refers to humans as well as non-humans, including, for example, mammals, birds, reptiles, amphibians, and fish. For instance, the non-humans may be mammals (e.g., a rodent, a mouse, a rat, a rabbit, a monkey, a dog, a cat, a primate, or a pig). In certain embodiments parenteral routes are desirable since they avoid contact with the digestive enzymes that are found in the alimentary canal. According to such embodiments, inventive compositions may be administered by injection (e.g., intravenous, subcutaneous or intramuscular, intraperitoneal injection), rectally, vaginally, topically (as by powders, creams, ointments, or drops), or by inhalation (as by sprays).

In a particular embodiment, the nanoparticles of the present invention are administered to a subject in need thereof systemically, e.g., parenterally, or by intravenous infusion or injection.

In some embodiments, a composition suitable for freezing is contemplated, including nanoparticles disclosed herein and a solution suitable for freezing, e.g., a sugar such as a mono, di, or poly saccharide, e.g. sucrose and/or a trehalose, and/or a salt and/or a cyclodextrin solution is added to the nanoparticle suspension. The sugar (e.g. sucrose or trehalose) may act, e.g., as a cryoprotectant to prevent the particles from aggregating upon freezing. For example, provided herein is a nanoparticle formulation comprising a plurality of disclosed nanoparticles, sucrose, an ionic halide, and water; wherein the nanoparticles/sucrose/water/ionic halide is about 3-40%/10-40%/20-95%/0.1-10% (w/w/w/w) or about 5-10%/10-15%/80-90%/1-10% (w/w/w/w). For example, such solution may include nanoparticles as disclosed herein, about 5% to about 20% by weight sucrose and an ionic halide such as sodium chloride, in a concentration of about 10-100 mM. In another example, provided herein is a nanoparticle formulation comprising a plurality of disclosed nanoparticles, trehalose, cyclodextrin, and water; wherein the nanoparticles/trehalose/water/cyclodextrin is about 3-40%/1-25%/20-95%/1-25% (w/w/w/w) or about 5-10%/1-25%/80-90%/10-15% (w/w/w/w). For example, such solution may include nanoparticles as disclosed herein, about 1% to about 25% by weight trehalose or sucrose (e.g. about 5% to about 25% trehalose or sucrose, e.g. about 10% trehalose or sucrose, or about 15% trehalose or sucrose, e.g. about 5% sucrose) by weight) and a cyclodextrin such as β-cyclodextrin, in a concentration of about 1% to about 25% by weight (e.g. about 5% to about 20%, e.g. 10% or about 20% by weight, or about 15% to about 20% by weight cyclodextrin). Comtemplated formulations may include a plurality of disclosed nanoparticles (e.g. nanoparticles having PLA-PEG and an active agent), and about 2% to about 15 wt % (or about 4% to about 6 wt %, e.g. about 5 wt %) sucrose and about 5 wt % to about 20% (e.g. about 7% wt percent to about 12 wt %, e.g. about 10 wt %) HPbCD).

The present disclosure relates in part to lyophilized pharmaceutical compositions that, when reconstituted, has a minimal amount of large aggregates. Such large aggregates may have a size greater than about 0.5 μm, greater than about 1 μm, or greater than about 10 μm, and can be undesirable in a reconstituted solution. Aggregate sizes can be measured using a variety of techniques including those indicated in the U.S. Pharmacopeia at 32 <788>, hereby incorporated by reference. The tests outlined in USP 32 <788> include a light obscuration particle count test, microscopic particle count test, laser diffraction, and single particle optical sensing. In one embodiment, the particle size in a given sample is measured using laser diffraction and/or single particle optical sensing.

The USP 32 <788> by light obscuration particle count test sets forth guidelines for sampling particle sizes in a suspension. For solutions with less than or equal to 100 mL, the preparation complies with the test if the average number of particles present does not exceed 6000 per container that are ≥10 μm and 600 per container that are ≥25 μm.

As outlined in USP 32 <788>, the microscopic particle count test sets forth guidelines for determining particle amounts using a binocular microscope adjusted to 100±10× magnification having an ocular micrometer. An ocular micrometer is a circular diameter graticule that consists of a circle divided into quadrants with black reference circles denoting 10 μm and 25 μm when viewed at 100× magnification. A linear scale is provided below the graticule. The number of particles with reference to 10 μm and 25 μm are visually tallied. For solutions with less than or equal to 100 mL, the preparation complies with the test if the average number of particles present does not exceed 3000 per container that are ≥10 μm and 300 per container that are ≥25 μm.

In some embodiments, a 10 mL aqueous sample of a disclosed composition upon reconstitution comprises less than 600 particles per ml having a size greater than or equal to 10 microns; and/or less than 60 particles per ml having a size greater than or equal to 25 microns.

Dynamic light scattering (DLS) may be used to measure particle size, but it relies on Brownian motion so the technique may not detect some larger particles. Laser diffraction relies on differences in the index of refraction between the particle and the suspension media. The technique is capable of detecting particles at the sub-micron to millimeter range. Relatively small (e.g., about 1-5 weight %) amounts of larger particles can be determined in nanoparticle suspensions. Single particle optical sensing (SPOS) uses light obscuration of dilute suspensions to count individual particles of about 0.5 μm. By knowing the particle concentration of the measured sample, the weight percentage of aggregates or the aggregate concentration (particles/mL) can be calculated.

Formation of aggregates can occur during lyophilization due to the dehydration of the surface of the particles. This dehydration can be avoided by using lyoprotectants, such as disaccharides, in the suspension before lyophilization. Suitable disaccharides include sucrose, lactulose, lactose, maltose, trehalose, or cellobiose, and/or mixtures thereof. Other contemplated disaccharides include kojibiose, nigerose, isomaltose, β,β-trehalose, α,β-trehalose, sophorose, laminaribiose, gentiobiose, turanose, maltulose, palatinose, gentiobiulose, mannobiase, melibiose, melibiulose, rutinose, rutinulose, and xylobiose. Reconstitution shows equivalent DLS size distributions when compared to the starting suspension. However, laser diffraction can detect particles of >10 μm in size in some reconstituted solutions. Further, SPOS also may detect >10 μm sized particles at a concentration above that of the FDA guidelines ($10^4$-$10^5$ particles/mL for >10 μm particles).

The present invention relates in part to the use of one or more ionic halide salts as an additional lyoprotectant to a sugar, such as sucrose, trehalose or mixtures thereof. Sugars may include disaccharides, monosaccharides, trisaccharides, and/or polysaccharides, and may include other excipients, e.g. glycerol and/or surfactants. Optionally, a cyclodextrin may be included as an additional lyoprotectant. The cyclodextrin may be added in place of the ionic halide salt. Alternatively, the cyclodextrin may be added in addition to the ionic halide salt.

Suitable ionic halide salts may include sodium chloride, calcium chloride, zinc chloride, or mixtures thereof. Additional suitable ionic halide salts include potassium chloride, magnesium chloride, ammonium chloride, sodium bromide, calcium bromide, zinc bromide, potassium bromide, magnesium bromide, ammonium bromide, sodium iodide, calcium iodide, zinc iodide, potassium iodide, magnesium iodide, or ammonium iodide, and/or mixtures thereof. In one embodiment, about 1 to about 15 weight percent sucrose may be used with an ionic halide salt. In one embodiment, the lyophilized pharmaceutical composition may comprise about 10 to about 100 mM sodium chloride. In another embodiment, the lyophilized pharmaceutical composition may comprise about 100 to about 500 mM of divalent ionic chloride salt, such as calcium chloride or zinc chloride. In yet another embodiment, the suspension to be lyophilized may further comprise a cyclodextrin, for example, about 1 to about 25 weight percent of cyclodextrin may be used.

Suitable cyclodextrin may include α-cyclodextrin, β-cyclodextrin, γ-cyclodextrin, or mixtures thereof. Exemplary cyclodextrins contemplated for use in the compositions disclosed herein include hydroxypropyl-β-cyclodextrin (HPbCD), hydroxyethyl-β-cyclodextrin, sulfobutylether-β-cyclodextrin, methyl-β-cyclodextrin, dimethyl-β-cyclodextrin, carboxymethyl-β-cyclodextrin, carboxymethyl ethyl-β-cyclodextrin, diethyl-β-cyclodextrin, tri-O-alkyl-β-cyclodextrin, glocosyl-β-cyclodextrin, and maltosyl-β-cyclodextrin. In one embodiment, about 1 to about 25 weight percent trehalose (e.g. about 10% to about 15%, e.g. 5 to about 20% by weight) may be used with cyclodextrin. In one embodiment, the lyophilized pharmaceutical composition may comprise about 1 to about 25 weight percent β-cyclodextrin. An exemplary composition may comprise nanoparticles comprising PLA-PEG, an active/therapeutic agent, about 4% to about 6% (e.g. about 5% wt percent) sucrose, and about 8 to about 12 weight percent (e.g. about 10 wt. %) HPbCD.

In one aspect, the invention provides a lyophilized pharmaceutical composition comprising polymeric nanoparticles, wherein upon reconstitution of the lyophilized pharmaceutical composition at a nanoparticle concentration of about 50 mg/mL, in less than or about 100 mL of an aqueous medium, the reconstituted composition suitable for parenteral administration comprises less than 6000, such as less than 3000, microparticles of greater than or equal to 10 microns; and/or less than 600, such as less than 300, microparticles of greater than or equal to 25 microns.

The number of microparticles can be determined by means such as the USP 32 <788> by light obscuration particle count test, the USP 32 <788> by microscopic particle count test, laser diffraction, and single particle optical sensing.

The nanoparticles may comprise a poly(lactic) acid-block-poly(ethylene)glycol copolymer or poly(lactic)-co-poly(glycolic) acid-block-poly(ethylene)glycol copolymer. For example, the poly(lactic) acid portion of the copolymer may have a weight average molecular weight of about 16 kDa and the poly(ethylene)glycol portion of the copolymer may have a weight average molecular weight of about 5 kDa.

The reconstituted composition may have minimal aggregation compared to a reconstituted composition that does not contain an ionic halide salt and/or a cyclodextrin. The reconstituted composition may have a polydispersity index of less than 0.2.

In an aspect, the invention provides a pharmaceutical composition suitable for parenteral use upon reconstitution, comprising a plurality of therapeutic particles each comprising a copolymer having a hydrophobic polymer segment and a hydrophilic polymer segment; an active agent; a sugar; and an ionic halide salt. The composition may further comprise a cyclodextrin.

The ionic halide salt may be selected from the group consisting of sodium chloride, calcium chloride, and zinc chloride, or mixtures thereof. In an embodiment, the pharmaceutical composition may comprise about 10 to about 100 mM sodium chloride. In another embodiment, the pharmaceutical composition may comprise about 100 to about 500 mM calcium chloride or zinc chloride.

In an aspect, the invention provides a pharmaceutical composition suitable for parenteral use upon reconstitution, comprising a plurality of therapeutic particles each comprising a copolymer having a hydrophobic polymer segment and a hydrophilic polymer segment; an active agent; a sugar; and a cyclodextrin.

The cyclodextrin may include α-cyclodextrin, β-cyclodextrin, γ-cyclodextrin, or mixtures thereof. In an embodiment, the pharmaceutical composition may comprise about 1 to about 25 weight percent β-cyclodextrin.

For example, the copolymer may be poly(lactic) acid-block-poly(ethylene)glycol copolymer. Upon reconstitution, a 100 mL aqueous sample may comprise less than 6000 particles having a size greater than or equal to 10 microns; and less than 600 particles having a size greater than or equal to 25 microns.

In another aspect, the invention provides a pharmaceutically acceptable formulation for parenteral administration, prepared by a process comprising: a) providing a composition comprising a plurality of therapeutic particles each comprising a copolymer having a hydrophobic polymer segment and a hydrophilic polymer segment; and an active agent; b) adding a disaccharide and an ionic halide salt to said composition; c) lyophilizing the composition to form a lyophilized composition; d) reconstituting the lyophilized composition to form the formulation suitable for parenteral administration. In an embodiment, a cyclodextrin is included in the formulation. In some embodiments, such reconstituting can advantageously be managed with simple manual mixing for a few minutes. The reconstituted product attributes (e.g. drug purity and/or release profile) may be substantially unchanged from a pre-lyophilized composition (e.g. suspension).

In yet another aspect, the invention provides a pharmaceutically acceptable formulation for parenteral administration, prepared by a process comprising: a) providing a composition comprising a plurality of therapeutic particles each comprising a copolymer having a hydrophobic polymer segment and a hydrophilic polymer segment; and an active agent; b) adding a disaccharide and a cyclodextrin to said composition; c) lyophilizing the composition to form a lyophilized composition; d) reconstituting the lyophilized composition to form the formulation suitable for parenteral administration. In some embodiments, such reconstituting can advantageously be managed with simple manual mixing for a few minutes. The reconstituted product attributes (e.g. drug purity and/or release profile) may be substantially unchanged from a pre-lyophilized composition (e.g. suspension).

The lyophilized composition may have a therapeutic particle concentration of greater than about 40 mg/mL. The formulation suitable for parenteral administration may have less than about 600 particles having a size greater than 10 microns in a 10 mL dose.

The step of adding a disaccharide and an ionic halide salt may comprise adding about 5 to about 15 weight percent sucrose or about 5 to about 20 weight percent trehalose (e.g., about 10 to about 20 weight percent trehalose), and about 10 to about 500 mM ionic halide salt. The ionic halide salt may be selected from sodium chloride, calcium chloride, and zinc chloride, or mixtures thereof. In an embodiment, about 1 to about 25 weight percent cyclodextrin is also added.

In another embodiment, the step of adding a disaccharide and a cyclodextrin may comprise adding about 5 to about 15 weight percent sucrose or about 5 to about 20 weight percent trehalose (e.g., about 10 to about 20 weight percent trehalose), and about 1 to about 25 weight percent cyclodextrin. In an embodiment, about 10 to about 15 weight percent cyclodextrin is added. The cyclodextrin may be selected from α-cyclodextrin, β-cyclodextrin, γ-cyclodextrin, or mixtures thereof.

The step of lyophilizing may comprise freezing the composition at a temperature of greater than about −40° C., or e.g. less than about −30° C., forming a frozen composition; and drying the frozen composition to form the lyophilized composition. The step of drying may occur at about 50 mTorr at a temperature of about −25 to about −34° C., or about −30 to about −34° C.

In another aspect, the invention provides a method of preventing substantial aggregation of particles in a pharmaceutical nanoparticle composition comprising adding a sugar and a salt to the lyophilized formulation to prevent aggregation of the nanoparticles upon reconstitution. In an embodiment, a cyclodextrin is also added to the lyophilized formulation. In yet another aspect, the invention provides a method of preventing substantial aggregation of particles in a pharmaceutical nanoparticle composition comprising adding a sugar and a cyclodextrin to the lyophilized formulation to prevent aggregation of the nanoparticles upon reconstitution.

EXAMPLES

The invention now being generally described, it will be more readily understood by reference to the following examples which are included merely for purposes of illustration of certain aspects and embodiments of the present invention, and are not intended to limit the invention in any way.

Example 1

Preparation of PLA-PEG

The synthesis is accomplished by ring opening polymerization of d,l-lactide with α-hydroxy-ω-methoxypoly(ethylene glycol) as the macro-initiator, and performed at an elevated temperature using Tin (II) 2-Ethyl hexanoate as a catalyst, as shown below (PEG Mn≈5,000 Da; PLA Mn≈16,000 Da; PEG-PLA $M_n$≈21,000 Da).

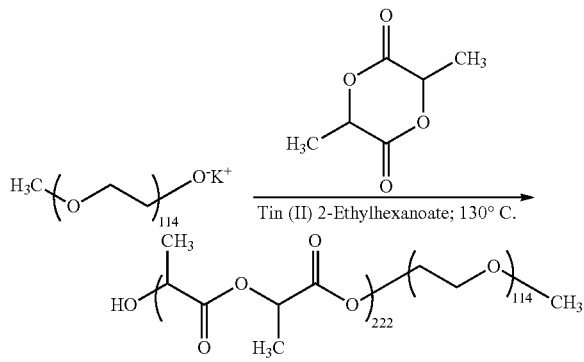

The polymer is purified by dissolving the polymer in dichloromethane, and precipitating it in a mixture of hexane and diethyl ether. The polymer recovered from this step is dried in an oven.

Example 2

Exemplary Nanoparticle Preparation—Emulsion Process

An organic phase is formed composed of a mixture of docetaxel (DTXL) and polymer (homopolymer, co-polymer, and co-polymer with ligand). The organic phase is mixed with an aqueous phase at approximately a 1:2 ratio (oil phase: aqueous phase) where the aqueous phase is composed of a surfactant (0.25% sodium cholate) and some dissolved solvent (4% ethyl acetate, 2% benzyl alcohol). In order to achieve high drug loading, about 30% solids in the organic phase is used.

The primary, coarse emulsion is formed by the combination of the two phases under simple mixing or through the use of a rotor stator homogenizer. The rotor/stator yields a homogeneous milky solution, while the stir bar produces a visibly larger coarse emulsion. It is observed that the stir bar method results in significant oil phase droplets adhering to the side of the feed vessel, suggesting that while the coarse emulsion size is not a process parameter critical to quality, it should be made suitably fine in order to prevent yield loss or phase separation.

Therefore the rotor stator is used as the standard method of coarse emulsion formation, although a high speed mixer may be suitable at a larger scale.

The primary emulsion is then formed into a fine emulsion through the use of a high pressure homogenizer. The size of the coarse emulsion does not significantly affect the particle size after successive passes (103) through the homogenizer.

After 2-3 passes the particle size is not significantly reduced, and successive passes can even cause a particle size increase. The organic phase is emulsified 5:1 O:W with standard aqueous phase, and multiple discreet passes are performed, quenching a small portion of emulsion after each pass. The indicated scale represents the total solids of the formulation.

The effect of scale on particle size shows scale dependence. The trend shows that in the 2-10 g batch size range, larger batches produce smaller particles. It has been demonstrated that this scale dependence is eliminated when considering greater than 10 g scale batches. The amount of solids used in the oil phase is about 30%.

Table A summarizes the emulsification process parameters.

TABLE A

| Parameter | Value |
| --- | --- |
| Coarse emulsion formation | High shear mixer |
| Homogenizer feed pressure | 2500 psi per chamber |
| Interaction chamber(s) | 4 × 200 μm Z-chamber |
| Number of homogenizer passes | 1 pass |
| Water phase [sodium cholate] | 0.25-0.35% |
| W:O ratio | 2:1 |
| [Solids] in oil phase | 30% |

The fine emulsion is then quenched by addition to deionized water at a given temperature under mixing. In the quench unit operation, the emulsion is added to a cold aqueous quench under agitation. This serves to extract a significant portion of the oil phase solvents, effectively hardening the nanoparticles for downstream filtration. Chilling the quench significantly improves drug encapsulation. The quench:emulsion ratio is approximately 5:1.

A solution of 35% (wt %) of Tween 80 is added to the quench to achieve approximately 4% Tween 80 overall After the emulsion is quenched a solution of Tween-80 is added which acts as a drug solubilizer, allowing for effective removal of unencapsulated drug during filtration. Table B indicates each of the quench process parameters.

TABLE B

Summary quench process parameters.

| Parameter | Value |
| --- | --- |
| Initial quench temperature | <5° C. |
| [Tween-80] solution | 35% |
| Tween-80:drug ratio | 25:1 |
| Q:E ratio | 10:1 |
| Quench hold/processing temp | ≤5° C. (with current 5:1 Q:E ratio, 25:1 Tween-80:drug ratio) |

The temperature must remain cold enough with a dilute enough suspension (low enough concentration of solvents) to remain below the $T_g$ of the particles. If the Q:E ratio is not high enough, then the higher concentration of solvent plasticizes the particles and allows for drug leakage. Conversely, colder temperatures allow for high drug encapsulation at low Q:E ratios (to ~3:1), making it possible to run the process more efficiently.

The nanoparticles are then isolated through a tangential flow filtration process to concentrate the nanoparticle suspension and buffer exchange the solvents, free drug, and drug solubilizer from the quench solution into water. A regenerated cellulose membrane is used with a molecular weight cutoffs (MWCO) of 300.

A constant volume diafiltration (DF) is performed to remove the quench solvents, free drug and Tween-80. To perform a constant-volume DF, buffer is added to the retentate vessel at the same rate the filtrate is removed. The process parameters for the TFF operations are summarized in Table C. Crossflow rate refers to the rate of the solution flow through the feed channels and across the membrane. This flow provides the force to sweep away molecules that can foul the membrane and restrict filtrate flow. The transmembrane pressure is the force that drives the permeable molecules through the membrane.

TABLE C

| TFF Parameters | |
| --- | --- |
| Parameter | Optimized Value |
| Membrane Material | Regenerated cellulose - Coarse Screen Membrane |
| Molecular Weight Cut off | 300 kDa |
| Crossflow Rate | 3.7-10 L/min/m² |
| Transmembrane Pressure | ~5 psid |
| Concentration of Nanoparticle Suspension for Diafiltration | 30-50 mg/ml |
| Number of Diavolumes | 20) |
| Membrane Area | 5 m²/kg |

The filtered nanoparticle slurry is then thermal cycled to an elevated temperature during workup. A small portion (typically 5-10%) of the encapsulated drug is released from the nanoparticles very quickly after its first exposure to 25° C. Because of this phenomenon, batches that are held cold during the entire workup are susceptible to free drug or drug crystals forming during delivery or any portion of unfrozen storage. By exposing the nanoparticle slurry to elevated temperature during workup, this 'loosely encapsulated' drug can be removed and improve the product stability at the expense of a small drop in drug loading. Table D summarizes two examples of 25° C. processing. Other experiments have shown that the product is stable enough after ~2-4 diavolumes to expose it to 25° C. without losing the majority of the encapsulated drug. 5 diavolumes is used as the amount for cold processing prior to the 25° C. treatment.

TABLE D

| | | Lots A | Lots B |
| --- | --- | --- | --- |
| Drug load | Cold workup | 11.3% | 9.7% |
| | 25° C. workup[1] | 8.7-9.1% | 9.0-9.9% |

TABLE D-continued

|  | | Lots A | Lots B |
|---|---|---|---|
| Stability[2] | Cold workup | <1 day | <1 day |
|  | 25° C. workup[1] | 5-7 days | 2-7 days |
| In vitro burst[3] | Cold workup | ~10% | Not performed |
|  | 25° C. workup[1] | ~2% |  |

[1] 25° C. workup sublots were exposed to 25° C. after at least 5 diavolumes for various periods of time. Ranges are reported because there were multiple sublots with 25° C. exposure.
[2] Stability data represents the time that final product could be held at 25° C. at 10-50 mg/ml nanoparticle concentrations prior to crystals forming in the slurry (visible by microscopy)
[3] In vitro burst represents the drug released at the first time point (essentially immediately)

After the filtration process, the nanoparticle suspension is passed through a sterilizing grade filter (0.2 μm absolute). Pre-filters are used to protect the sterilizing grade filter in order to use a reasonable filtration area/time for the process. Values are as summarized in Table E.

TABLE E

| Parameter | O Value | Effect |
|---|---|---|
| Nanoparticle Suspension Concentration | 50 mg/ml | Yield losses are higher at higher [NP], but the ability to filter at 50 mg/ml obviates the need to aseptically concentrate after filtration |
| Filtration flow rate | ~1.3 L/min/m² | Filterability decreases as flow rate increases |

The pre-filter has Seitz PDD1 depth filter media in Pall SUPRAcap or Stax filter cartridges. 0.2 m² of filtration surface area per kg of nanoparticles for depth filters and 1.3 m² of filtration surface area per kg of nanoparticles for the sterilizing grade filters can be used.

Example 3

Lyophilized Composition with Sugar and Salt

Figure 3:
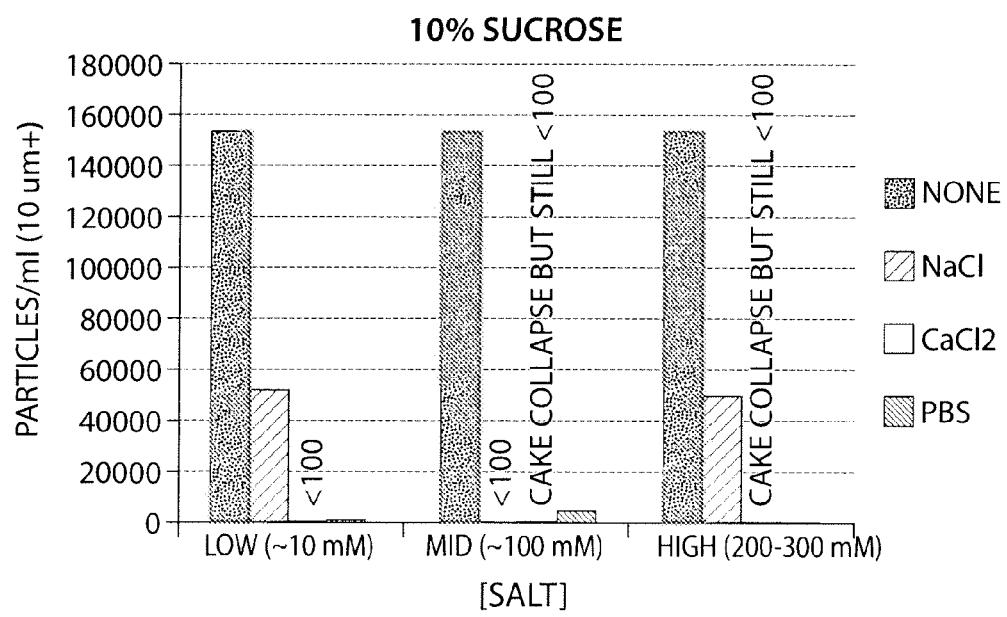
FIG. 3 depicts the effect of salt concentration and sucrose on particle size in reconstituted nanoparticle suspensions.

As shown in FIG. 3, nanoparticle suspensions with >40 mg/mL nanoparticle concentrations (with nanoparticles formed as in Example 2, with 16/5 PLA-PEG as the polymer) are lyophilized in the presence of 10% sucrose and an additive: NaCl, $CaCl_2$, or PBS. This experiment formulates nanoparticle suspensions at high (>40 mg/ml) nanoparticle concentrations that can be reconstituted without microaggregation. All three $CaCl_2$ formulations produce reconstituted cakes with <100 particles/ml (10 μm+), even in the mid (150 mM) and high (200 mM) concentration ranges which produced a lyophilisate that had collapsed.

Lower concentrations of salt behave similarly as in the absence of salt. Higher concentrations of salt generally show much higher particle concentrations.

Example 4

Lyophilized Composition with Sugar and/or Salt and/or Cyclodextrin

Nanoparticle suspensions are lyophilized in the presence of a sugar (e.g. sucrose or trehalose), salt (e.g. NaCl or $CaCl_2$), and/or cyclodextrin (e.g. hydroxypropyl beta cyclodextrin—HPbCD). For example, formulations are prepared with 250 mM or 500 mM of NaCl or $CaCl_2$; and/or with 15%, 20% or 25% by weight sucrose or trehalose, for example, 20% by weight trehalose, 500 mM $CaCl_2$, 5% HPbCd. Representative formulations are shown in Table F.

Table F indicates particles counted and sized one at a time over a large size range by an AccuSizer, and counted the larger size of particle numbers to find the aggregates that existed in formulation. Table F shows the number of particles after reconstituting solution using distilled water into lyophilized cakes. In the Table F, F/T samples are from freezing and thawing only without drying, whereas vial number from 1 to 4 as well as tall vial 1 and 2 were from lyophilized samples. Most of formulations except $CaCl_2$ 500 mM with 15% Trehalose showed low number of particle aggregates and subsequent tests were done to optimize the formulations.

TABLE F

| | | Particle Number/ml (larger than 10 μm) | | | | | | |
|---|---|---|---|---|---|---|---|---|
| Formulation | Reconstitution | F/T control | 1 | 2 | 3 | 4 | Tall vial 1 | Tall Vial 2 |
| $CaCl_2$ + 15% sucrose | Good | 282 | 527 | 333 | 940 | 396 | 1110 | 430 |
| $CaCl_2$ + 15% trehalose | Dissolved right away | 310 | 17600 | 548 | Vial broke | 1160000 | 1190 | 442 |
| $CaCl_2$ + 20% trehalose + 5% HPbCD | quick | 945 | 446 | 670 | 486 | 3500 | 384 | 713 |
| 20% trehalose + 10% HPbCD | quick | 392 | 28300 | 4210 | 899 | 2790 | 239 | 75.5 |

Example 5

Lyophilized Composition with Sugar and/or Salt and/or Cyclodextrin

Nanoparticle suspensions are lyophilized in the presence of a sugar (e.g. trehalose), cyclodextrin (e.g. hydroxypropyl beta cyclodextrin—HPbCD), and/or salt (e.g. $CaCl_2$). The excipient and level to screen formulations using Design of Experiment (DOE) are listed below in Table G. Tall vials are used for all formulations with a fill volume of 5 mL (n=5-6 vials per formulation). Primary drying is performed at −37° C. shelf temperature.

TABLE G

| Excipient | Level 1 | Level 2 | Level 3 | Level 4 |
|---|---|---|---|---|
| HPbCD | 5% | 10% | N/A | N/A |
| Trehalose | 10% | 20% | N/A | N/A |
| $CaCl_2$ | 0 mM | 100 mM | 250 mM | 500 mM |

The appearance of the lyophilized formulations and their reconstitution properties are listed below in Table H. In all the formulations tested, the appearance of the formulations is at least partially melted.

hydroxypropyl beta cyclodextrin—HPbCD). The formulations tested are listed below in Table H. Tall vials are used for all formulations with a fill volume of 5 mL (n=10 vials per formulation).

TABLE H

| Formulation | Appearance Post Lyophilization | Reconstitution |
| --- | --- | --- |
| 5% HPbCD | partially melted back | OK, very turbid |
| 10% HPbCD | partially melted back | OK |
| 10% Trehalose + 10% HPbCD | partially melted back | Required lots of vortexing |
| 10% Trehalose + 5% HPbCD | partially melted back | Required lots of vortexing |
| 20% Trehalose + 10% HPbCD | partially melted back | Required lots of vortexing |
| 20% Trehalose + 5% HPbCD | partially melted back | No, small chunks remain |
| CaCl2 100 mM + 10% Trehalose + 10% HPbCD | partially melted back | Required lots of vortexing |
| CaCl2 100 mM + 10% Trehalose + 5% HPbCD | partially melted back | Required lots of vortexing |
| CaCl2 100 mM + 20% Trehalose + 10% HPbCD | partially melted back | Required tons of vortexing |
| CaCl2 100 mM + 20% Trehalose + 5% HPbCD | B&E completely collapsed; A/C/D partially | NO, large chunks remain |
| CaCl2 250 mM + 10% Trehalose + 10% HPbCD | partially melted back | Required lots of vortexing |
| CaCl2 250 mM + 10% Trehalose + 5% HPbCD | A collapsed; others partially melted back | Yes, with no mixing |
| CaCl2 250 mM + 20% Trehalose + 10% HPbCD | partially melted back | Required lots of vortexing |
| CaCl2 250 mM + 20% Trehalose + 5% HPbCD | partially melted back | Required tons of vortexing |
| CaCl2 500 mM + 10% Trehalose + 10% HPbCD | partially melted back | Required tons of vortexing |
| CaCl2 500 mM + 10% Trehalose + 5% HPbCD | Mostly collapsed | No-Required tons of vortexing AND time |
| CaCl2 500 mM + 20% Trehalose + 10% HPbCD | Mostly collapsed | Required tons of vortexing |
| CaCl2 500 mM + 20% Trehalose + 5% HPbCD | Mostly collapsed and partially blown up | Required tons of vortexing AND time |

Figure 4:
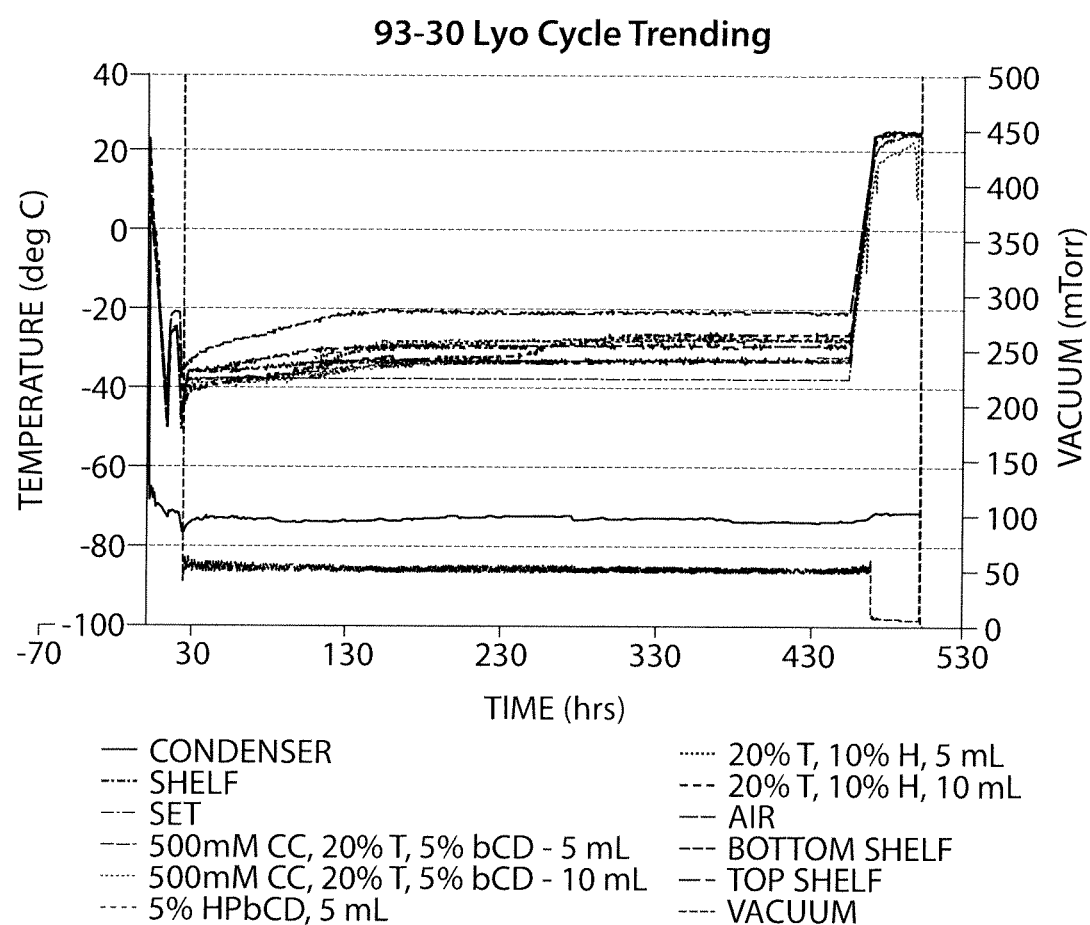
FIG. 4 depicts temperature cycling for various lypholization formulations.

Cycle data is shown in FIG. 4, and shows lyophilization process parameters: shelf temperature, product temperature, chamber pressure and time. These process parameters are controlled from the time the product is first placed on the lyophilizer shelves during loading until the product is removed. Conditions reflected in the chart illustrate the process parameters for one of respective lyo run to screen HPbCD concentration.

Figure 5:
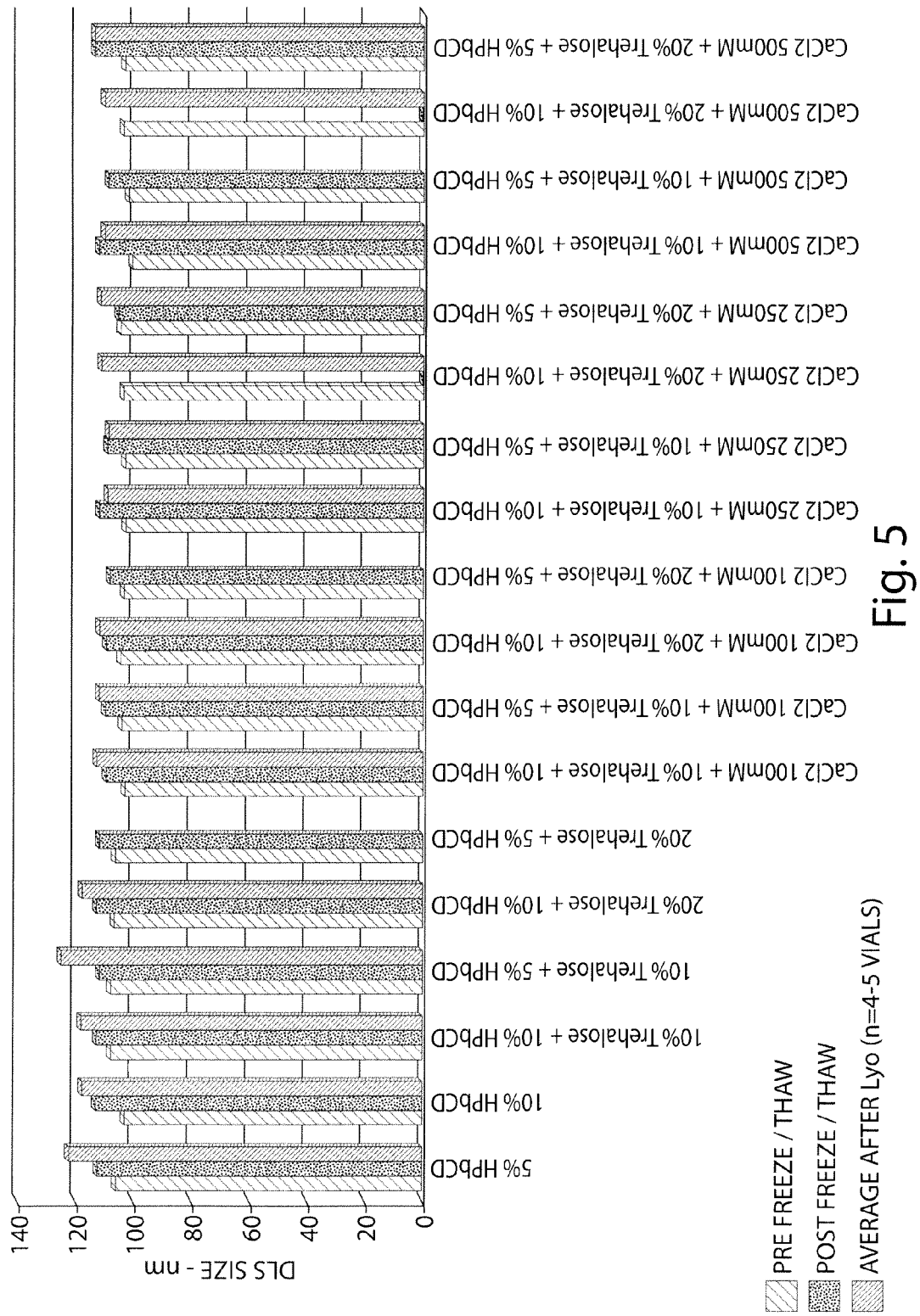
FIG. 5 depicts the sizes via dynamic light scattering (DLS) of the various reconstituted nanoparticle suspensions disclosed herein.

The sizes of the particles in the various lyophilized formulations are measured by dynamic light scattering (DLS) and shown in FIG. 5. In all the formulations tested, the nanoparticle size increased after freeze/thaw and lyophilization as compared to pre-frozen samples.

Figure 6:
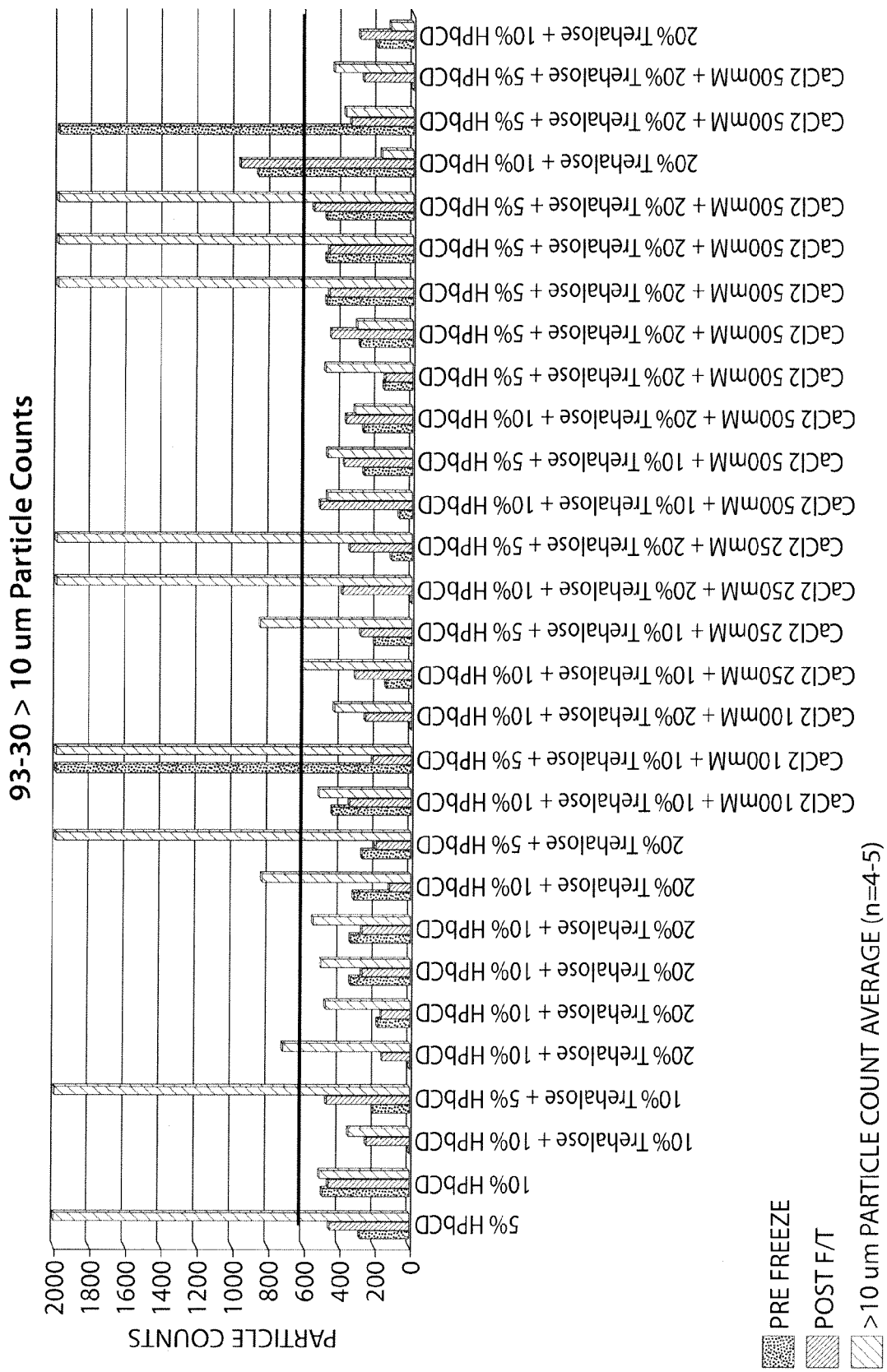
FIG. 6 depicts the particulate counts of the various reconstituted nanoparticle suspensions disclosed herein

The number of microparticles greater than 10 µm in the various formulations are measured by microscopic particle count test and shown in FIG. 6. In general, formulations comprising higher concentrations of cyclodextrin exhibit better particulate counts.

Example 5

Lyophilized Composition with Sugar and Cyclodextrin

Nanoparticle suspensions are lyophilized in the presence of a sugar (e.g. trehalose or sucrose) and cyclodextrin (e.g.

TABLE H

| Excipient | Level 1 | Level 2 | Level 3 | Level 4 |
| --- | --- | --- | --- | --- |
| HPbCD | 10% | 15% | 20% | NA |
| Trehalose | 0% | 5% | 10% | 20% |

| Alternative Variable | Levels | Formulation(s) | | |
| --- | --- | --- | --- | --- |
| Sugar Type | Sucrose | 1) 10% HPbCD, 10% Sucrose | | |
| | | 2) 10% HPbCD, 5% Sucrose | | |

The appearance of the lyophilized formulations and their reconstitution properties are listed below in Table I. Increased concentration of trehalose and cyclodextrin appeared to result in poorer reconstitution properties. In all the formulations tested, the DLS sizes increased after freeze/thaw but decreased after lyophilization.

TABLE I

| Formulation | DXTL Conc (mg/ml) | Appearance Post Lyophilization | Reconstitution |
|---|---|---|---|
| 0% Trehalose, 10% HPbCD | 4.803 | partially melted back | ok - manual mixing required (<1 min) |
| 0% Trehalose, 15% HPbCD | 4.711 | partially melted back | ok - manual mixing required (<1 min ea) - some 1g chunks to disperse |
| 0% Trehalose, 20% HPbCD | 4.736 | partially melted back | Lots of manual mixing required (couple of min) |
| 5% Trehalose, 10% HPbCD | 4.328 | partially melted back | majority reconstituted immediate but some sm chunks needed additional mixing |
| 5% Trehalose, 15% HPbCD | 4.674 | partially melted back | some reconstituted immediately but more chunks than −4 which needed extra mixing |
| 5% Trehalose, 20% HPbCD | 4.23 | partially melted back | majority reconstituted immediate but some sm chunks needed additional mixing |
| 10% Trehalose, 10% HPbCD | 4.28 | partially melted back | majority reconstituted immediate, a bit of extra mixing |
| 10% Trehalose, 15% HPbCD | 4.637 | partially melted back | majority reconstituted immediate, a bit of extra mixing |
| 10% Trehalose, 20% HPbCD | 4.158 | partially melted back | some reconstituted quickly but had to do extra mixing to get chunks in |
| 20% Trehalose, 10% HPbCD | 3.655 | partially melted back | Had chunks but reconstitued with shaking |
| 20% Trehalose, 15% HPbCD | 3.397 | partially melted back | Had chunks but reconstitued with 1.5 min shaking |
| 20% Trehalose, 20% HPbCD | 4.392 | partially melted back | Had chunks but reconstitued with 2 min shaking |
| 5% Sucrose, 10% HPbCD | 4.614 | partially melted back | reconstituted ok within ½ min shaking (probably less) |
| 10% Sucrose, 10% HPbCD | 4.686 | partially melted back | reconstituted ok within ½ min shaking (probably less) |

Figure 7:
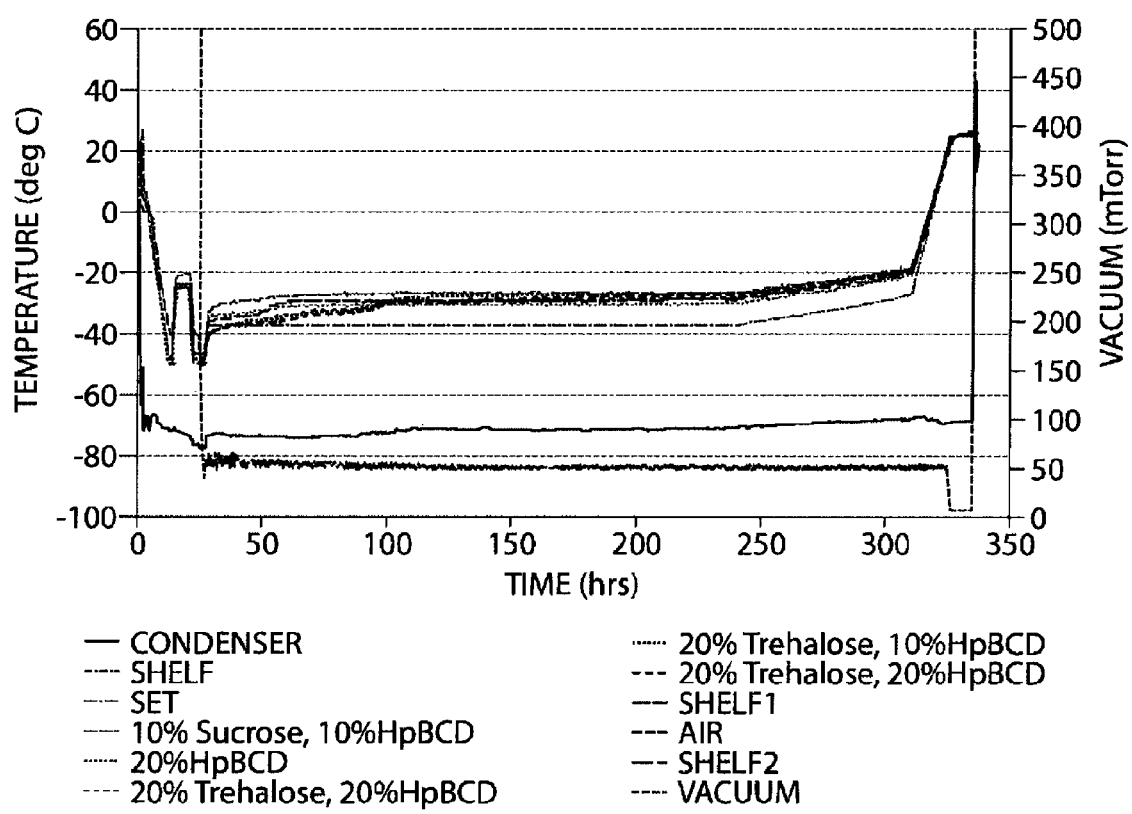
FIG. 7 depicts temperature cycling for various lypholization formulations.
Figure 8:
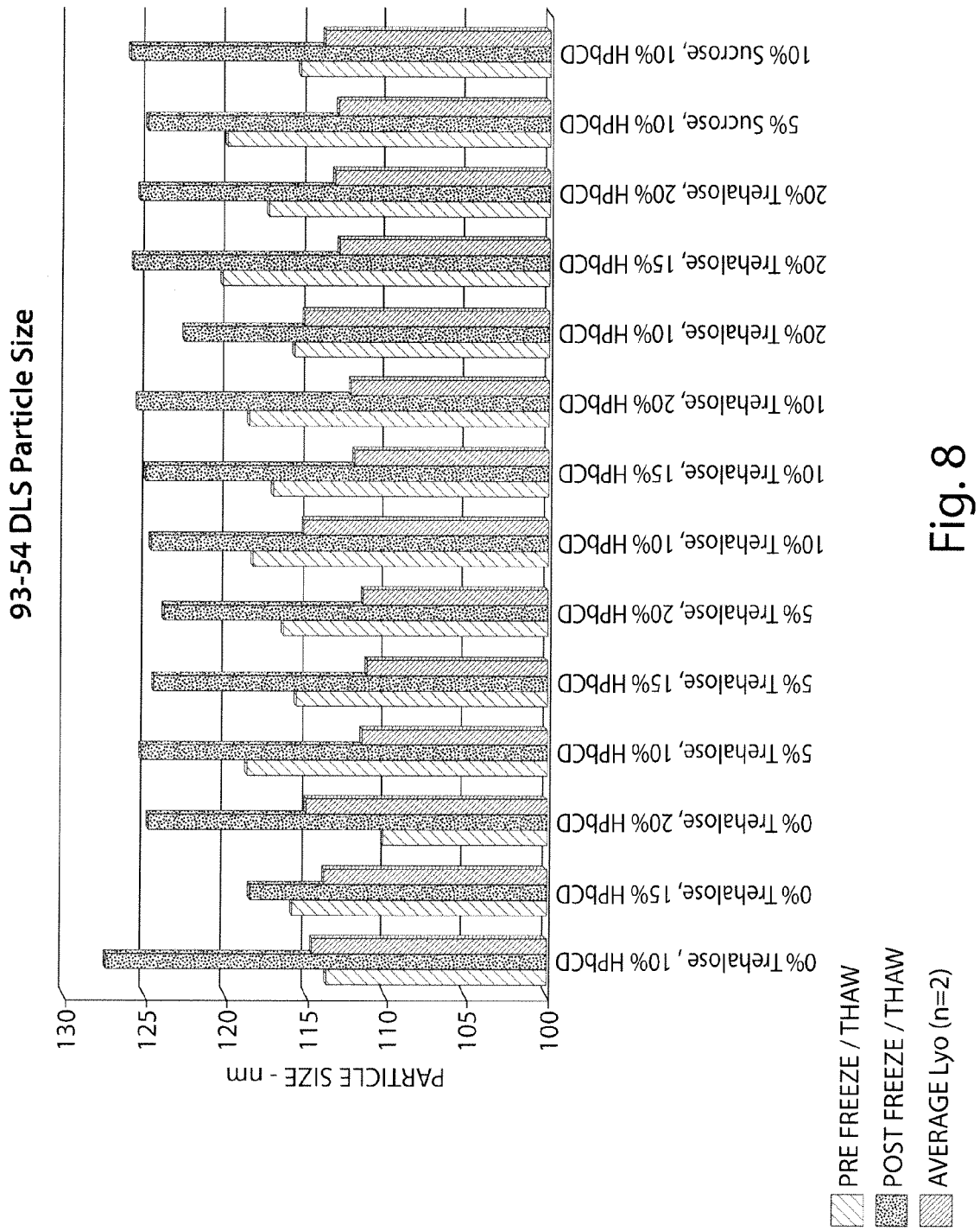
FIG. 8 depicts nanoparticle sizes (measured using DLS) of the various reconstituted nanoparticle suspensions disclosed herein.

Cycle data is shown in FIG. 7. The size of the particles in the various lyophilized formulations are measured by dynamic light scattering (DLS) and shown in FIG. 8.

Figure 9:
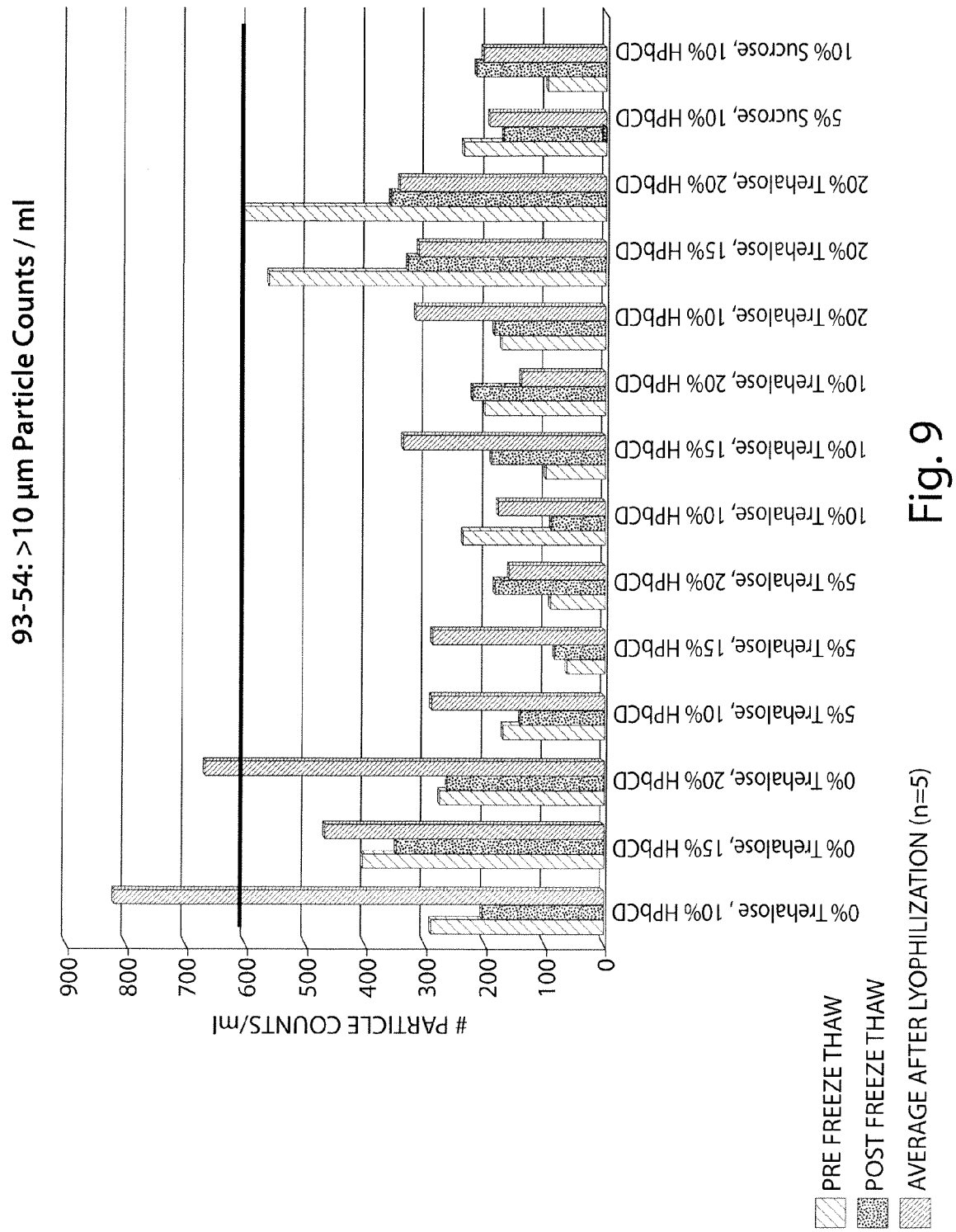
FIG. 9 depicts the particulate counts of the various reconstituted nanoparticle suspensions disclosed herein.
Figure 10:
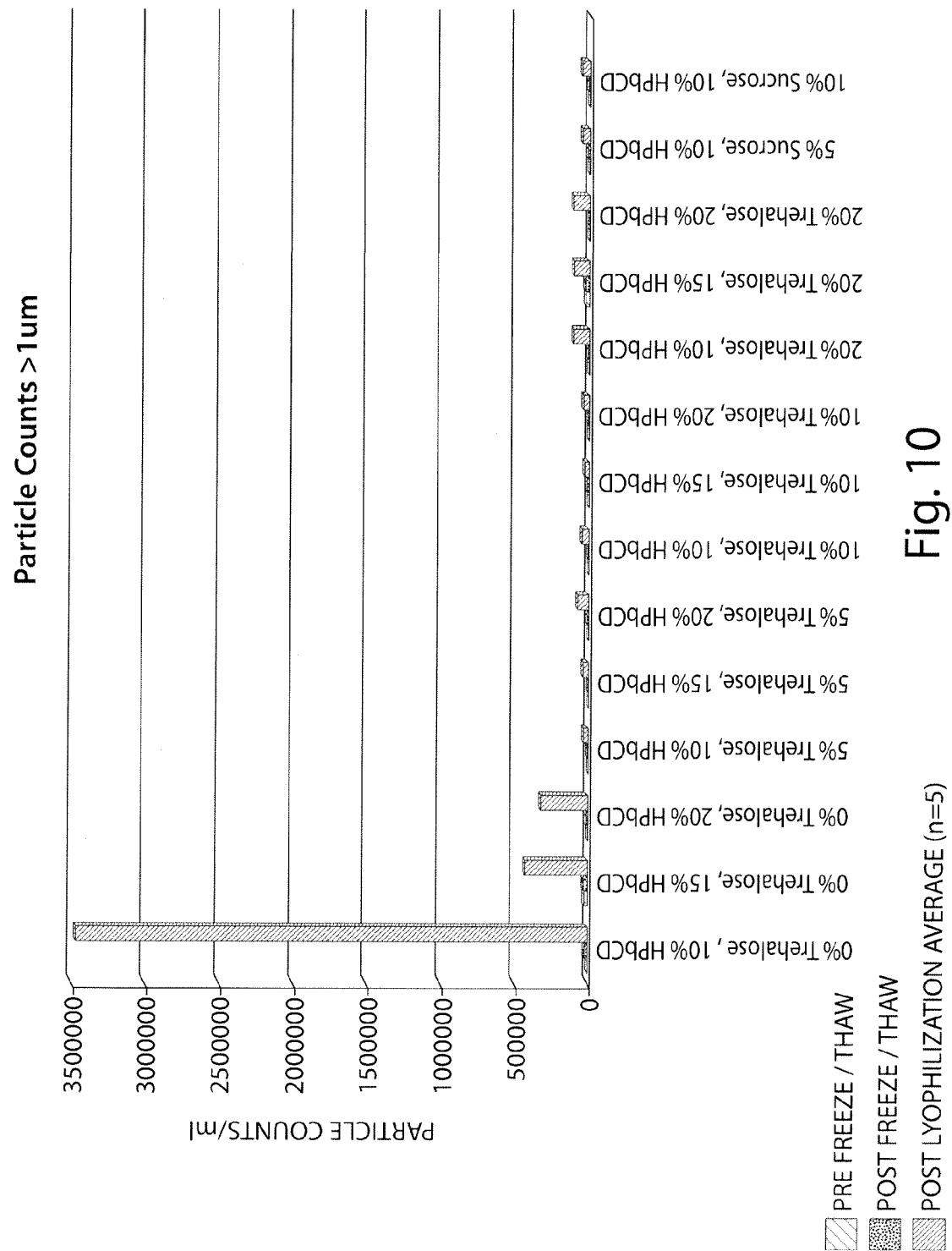
FIG. 10 depicts the particulate counts of the various reconstituted nanoparticle suspensions disclosed herein.
Figure 11:
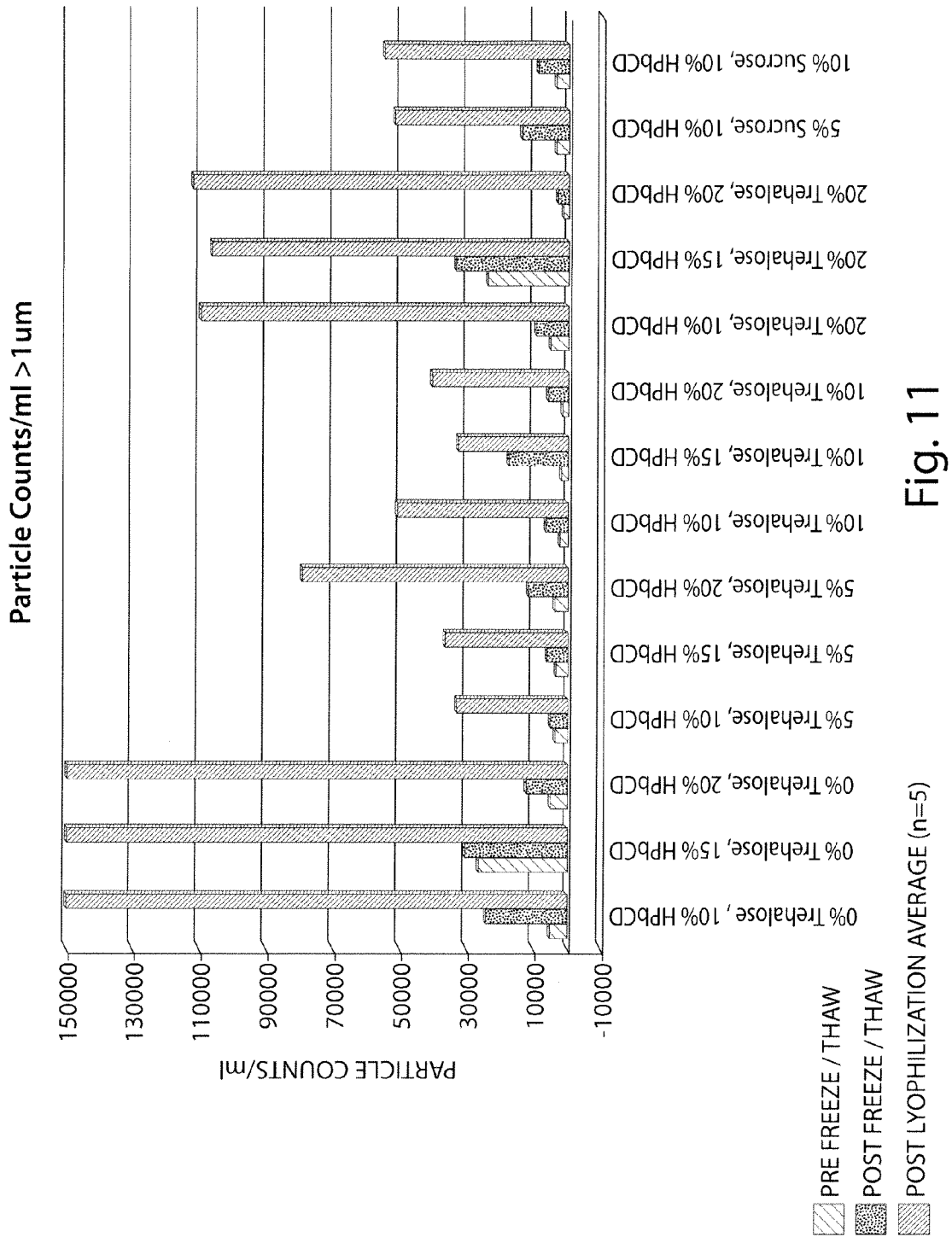
FIG. 11 depicts the particulate counts of the various reconstituted nanoparticle suspensions disclosed herein.

The number of microparticles per ml which are greater than 10 μm in the various formulations are measured by microscopic particle count test as shown in FIG. 9. Almost all the formulations tested are below the USP 32 <788> limit. The number of microparticles which are greater than 1 μm in the various formulations are shown in FIGS. 10 and 11. In most formulations, the number of microparticles greater than 1 μm is increased in the lyophilized samples when compared to the pre-frozen or freeze/thaw samples.

Figure 12:
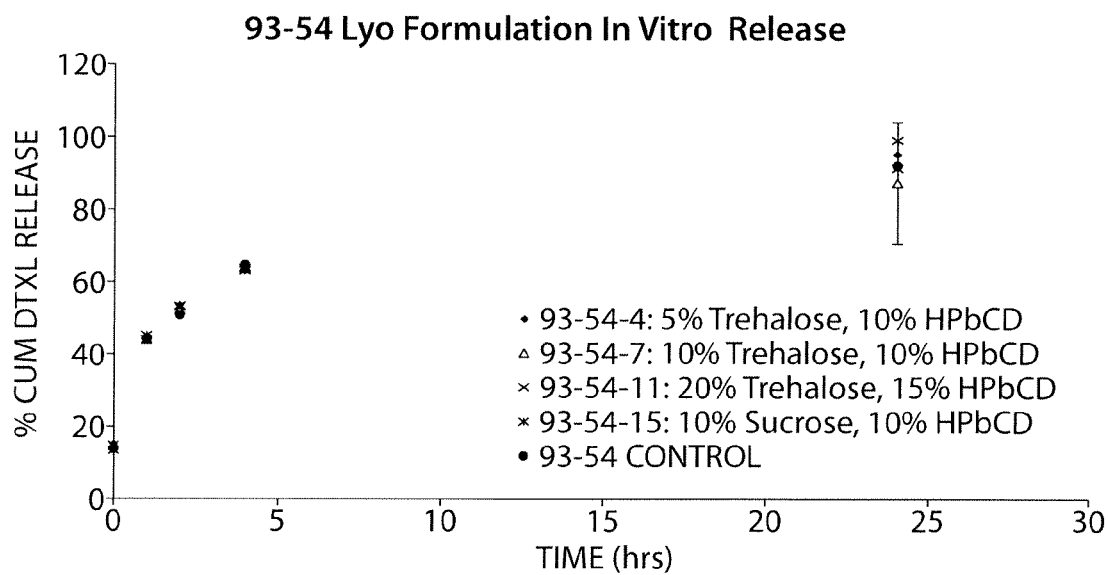
FIG. 12 depicts in vitro release of docetaxel of various nanoparticle suspensions disclosed herein.
Figure 13:
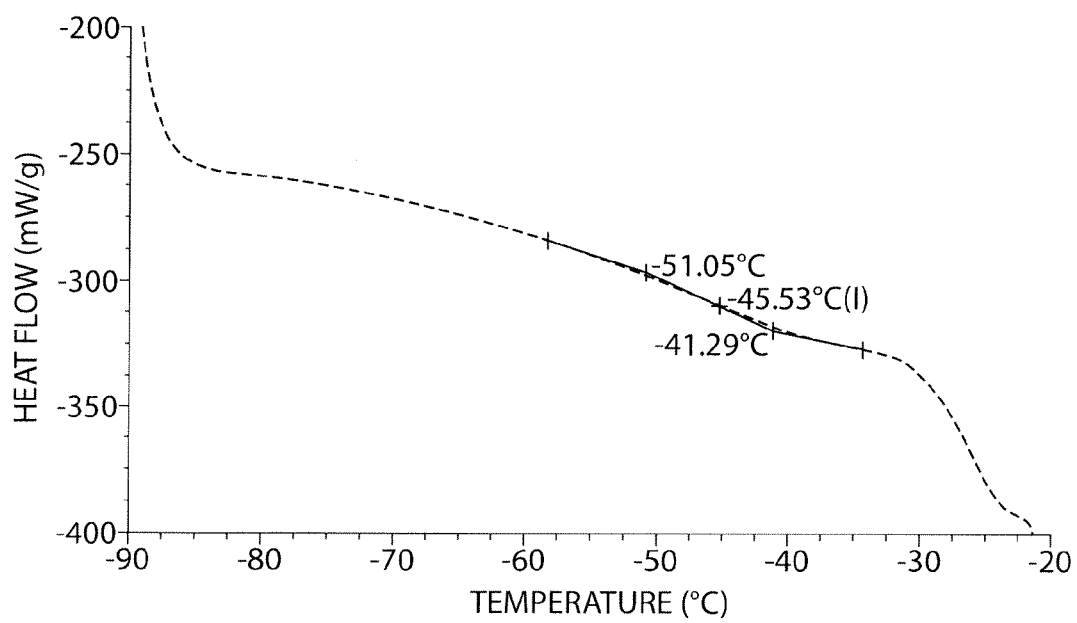
FIG. 13 depicts a differential scanning calorimetry (DSC) measurement of nanoparticle suspensions having 5% trehalose and 10% hydroxypropylcyclodextrin.
Figure 14:
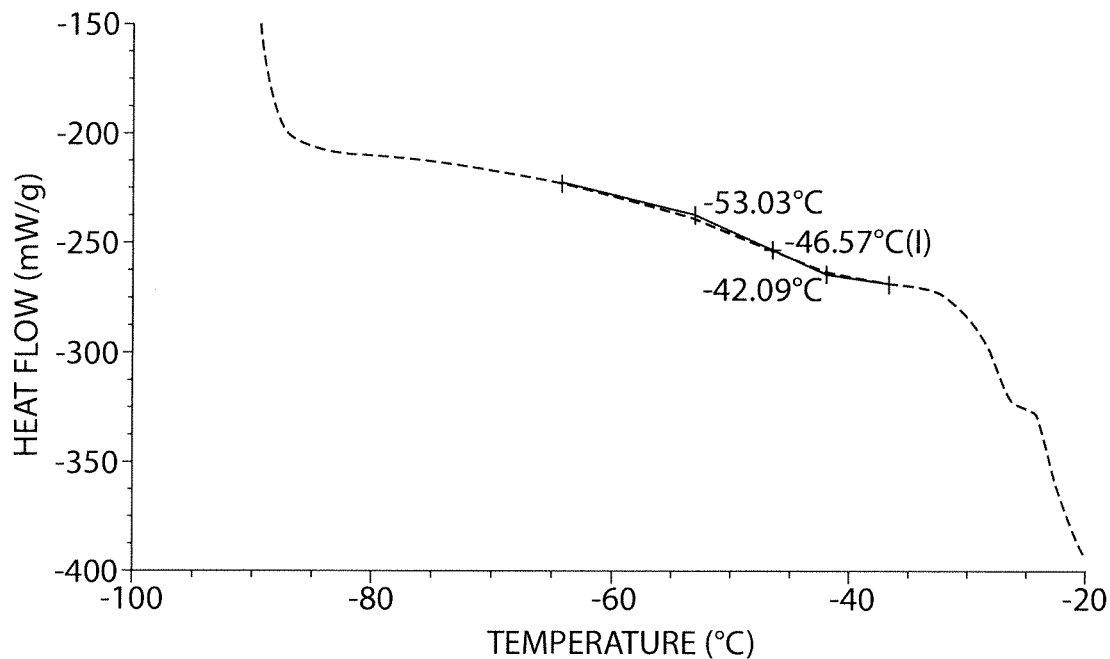
FIG. 14 depicts the DSC properties of nanoparticle suspensions having 10% trehalose and 10% hydroxypropylcyclodextrin.
Figure 15:
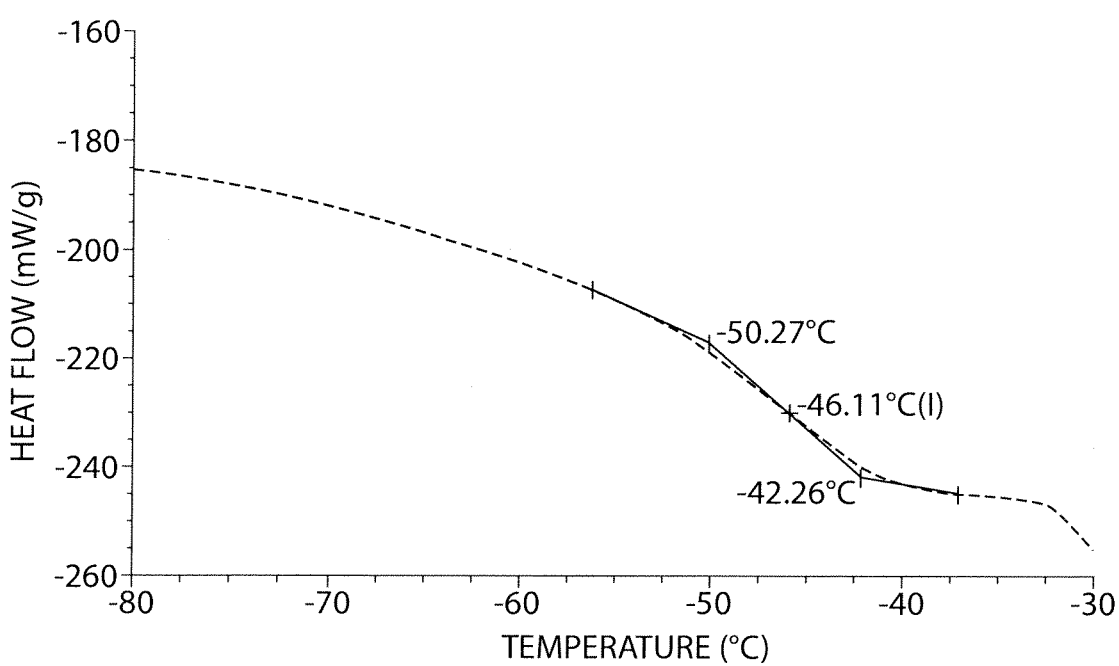
FIG. 15 depicts the DSC properties of nanoparticle suspensions having 20% trehalose and 15% hydroxypropylcyclodextrin.
Figure 16:
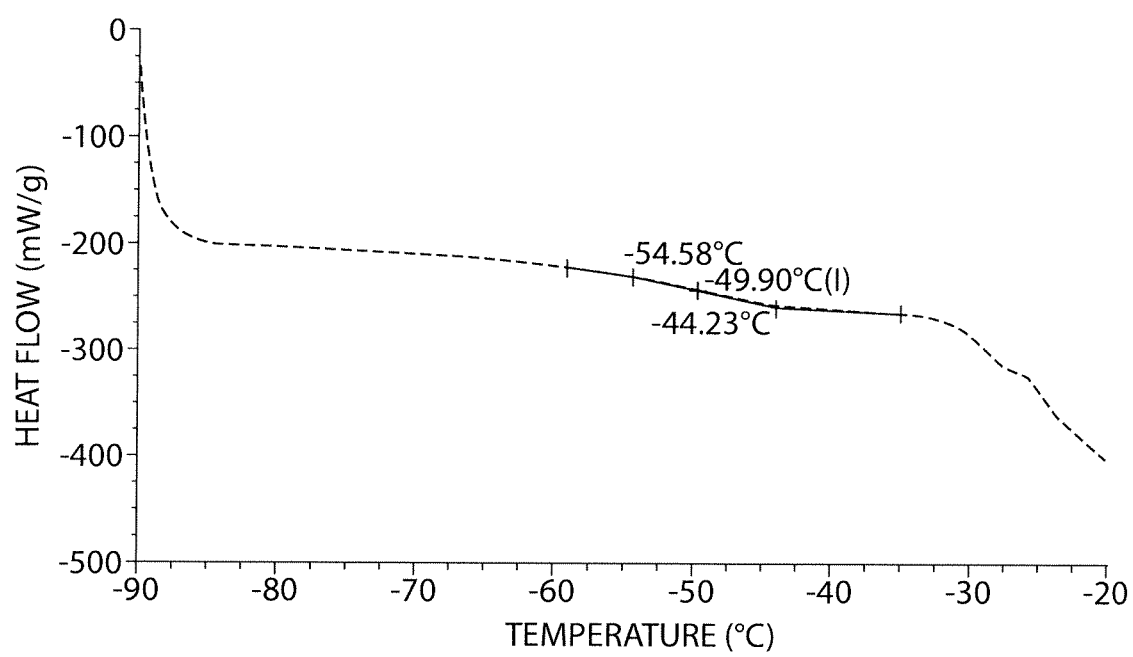
FIG. 16 depicts the DSC properties of nanoparticle suspensions having 10% sucrose and 10% hydroxypropylcyclodextrin.

In vitro release test is performed on docetaxel nanoparticles lyophilized in the presence of sugar and cyclodextrin. Results are depicted in FIG. 12.

Differential scanning calorimetry is also performed on various nanoparticle formulations as depicted in FIGS. 13-16.

EQUIVALENTS

Those skilled in the art will recognize, or be able to ascertain using no more than routine experimentation, many equivalents to the specific embodiments of the invention described herein. Such equivalents are intended to be encompassed by the following claims.

INCORPORATION BY REFERENCE

The entire contents of all patents, published patent applications, websites, and other references cited herein are hereby expressly incorporated herein in their entireties by reference.

The invention claimed is:

1. A reconstituted lyophilized pharmaceutical composition suitable for parenteral administration comprising:
   a 10-100 mg/mL concentration of polymeric nanoparticles in an aqueous medium; wherein the polymeric nanoparticles comprise: a poly(lactic) acid-block-poly(ethylene)glycol copolymer or poly(lactic)-co-poly(glycolic) acid-block-poly(ethylene)glycol copolymer, and a taxane agent;
   4 to 6 weight percent sucrose or trehalose; and
   7 to 12 weight percent hydroxypropyl β-cyclodextrin.

2. The reconstituted lyophilized pharmaceutical composition of claim 1, wherein the reconstituted lyophilized pharmaceutical composition comprises:
   less than 6000 microparticles of greater than or equal to 10 microns; and
   less than 600 microparticles of greater than or equal to 25 microns; per sample container having less than or about 100 mL of the composition.

3. The reconstituted lyophilized pharmaceutical composition of claim 1, wherein a container having about 100 mL of the composition of the reconstituted composition comprises less than 3000 microparticles having a size greater than or equal to 10 microns; and less than 300 microparticles having a size greater than or equal to 25 microns.

4. The reconstituted lyophilized pharmaceutical composition of claim 1, wherein a 10 mL aqueous sample of said composition has less than 600 particles having a size greater than or equal to 10 microns per mL of the aqueous sample.

5. The reconstituted lyophilized pharmaceutical composition of claim 1, wherein the poly(lactic) acid portion of the copolymer has a weight average molecular weight of about 16 kDa and the poly(ethylene)glycol portion of the copolymer has a weight average molecular weight of about 5 kDa.

6. The reconstituted lyophilized pharmaceutical composition of claim 5, wherein the taxane is docetaxel.

7. The reconstituted lyophilized pharmaceutical composition of claim 1, wherein the taxane is docetaxel.

8. The reconstituted lyophilized pharmaceutical composition of claim 1, comprising about 4 to 6 weight percent sucrose.

9. The reconstituted lyophilized pharmaceutical composition of claim 1, wherein the reconstituted composition has minimal aggregation compared to a reconstituted composition that does not contain hydroxypropyl β cyclodextrin.

10. The reconstituted lyophilized pharmaceutical composition of claim 1, comprising about 40-60 mg/mL concentration of polymeric nanoparticles.

11. The reconstituted lyophilized pharmaceutical composition of claim 1, wherein the polymeric nanoparticles have a diameter of about 60 nm to about 140 nm.

12. A pharmaceutically acceptable aqueous solution comprising:
   about 40-60 mg/mL polymeric nanoparticles, wherein the nanoparticles comprise a poly(lactic) acid-block-poly(ethylene)glycol copolymer or poly(lactic)-co-poly(glycolic) acid-block-poly(ethylene)glycol copolymer, and a taxane;
   about 7 to about 12 weight percent hydroxypropyl β-cyclodextrin; and
   about 4 to about 6 weight percent sucrose.

13. A reconstituted lyophilized pharmaceutical composition suitable for parenteral administration comprising:
   a 10-100 mg/mL concentration of polymeric nanoparticles in an aqueous medium;
   wherein the polymeric nanoparticles comprise: a poly(lactic) acid-block-poly(ethylene)glycol copolymer and docetaxel;
   4 to 6 weight percent sucrose or trehalose; and
   7 to 12 weight percent hydroxypropyl β-cyclodextrin.

14. The reconstituted lyophilized pharmaceutical composition of claim 13, wherein the reconstituted lyophilized pharmaceutical composition comprises:
   less than 6000 microparticles of greater than or equal to 10 microns; and
   less than 600 microparticles of greater than or equal to 25 microns; per sample container having less than or about 100 mL of the composition.

15. The reconstituted lyophilized pharmaceutical composition of claim 13, wherein a container having about 100 mL of the reconstituted composition comprises less than 3000 microparticles having a size greater than or equal to 10 microns; and less than 300 microparticles having a size greater than or equal to 25 microns.

16. The reconstituted lyophilized pharmaceutical composition of claim 13, wherein a 10 mL aqueous sample of said composition has less than 600 particles having a size greater than or equal to 10 microns per mL of the aqueous sample.

17. The reconstituted lyophilized pharmaceutical composition of claim 13, wherein the poly(lactic) acid portion of the copolymer has a weight average molecular weight of about 16 kDa and the poly(ethylene)glycol portion of the copolymer has a weight average molecular weight of about 5 kDa.

18. The reconstituted lyophilized pharmaceutical composition of claim 17, wherein the polymeric nanoparticles have a diameter of about 60 nm to about 140 nm.

19. The reconstituted lyophilized pharmaceutical composition of claim 18, comprising about 4 to 6 weight percent sucrose.

* * * * *